US011510957B2

(12) United States Patent
Huang et al.

(10) Patent No.: US 11,510,957 B2
(45) Date of Patent: Nov. 29, 2022

(54) METHOD FOR TREATING OR ALLEVIATING AUTOIMMUNE-RELATED DISEASES

(71) Applicant: Industrial Technology Research Institute, Hsinchu (TW)

(72) Inventors: Kuo-Kuei Huang, Zhudong Township (TW); I-Horng Pan, Zhubei (TW); Meng-Nan Lin, Zhubei (TW); Jir-Mehng Lo, Guanxi Township (TW); Jennline Sheu, Hsinchu (TW); Pei-Ru Liau, Taoyuan (TW); Yi-Cheng Cheng, Hsinchu (TW); Pei-Hsin Lin, Hsinchu (TW)

(73) Assignee: INDUSTRIAL TECHNOLOGY RESEARCH INSTITUTE, Hsinchu (TW)

(*) Notice: Subject to any disclaimer, the term of this patent is extended or adjusted under 35 U.S.C. 154(b) by 0 days.

(21) Appl. No.: 16/698,502

(22) Filed: Nov. 27, 2019

(65) Prior Publication Data
US 2020/0121753 A1 Apr. 23, 2020

Related U.S. Application Data

(62) Division of application No. 15/416,304, filed on Jan. 26, 2017, now abandoned.

(60) Provisional application No. 62/287,345, filed on Jan. 26, 2016.

(51) Int. Cl.
*A61K 36/00* (2006.01)
*A61K 36/9064* (2006.01)
*A61K 31/11* (2006.01)
*A61K 9/00* (2006.01)

(52) U.S. Cl.
CPC ........ *A61K 36/9064* (2013.01); *A61K 9/0019* (2013.01); *A61K 9/0024* (2013.01); *A61K 9/0053* (2013.01); *A61K 9/0073* (2013.01); *A61K 31/11* (2013.01); *A61K 2236/333* (2013.01)

(58) Field of Classification Search
None
See application file for complete search history.

(56) References Cited

U.S. PATENT DOCUMENTS

| 7,390,512 | B2 | 6/2008 | Rangel |
| 9,283,204 | B2 | 3/2016 | Ip et al. |
| 2008/0311230 | A1 | 12/2008 | Omer |
| 2013/0338199 | A1 | 12/2013 | Saxena et al. |

FOREIGN PATENT DOCUMENTS

| CN | 101269198 A | 9/2008 |
| CN | 102048714 A | 5/2011 |
| CN | 102716407 A | 10/2012 |
| CN | 103271271 A | 9/2013 |
| CN | 103330099 A | 10/2013 |
| KR | 10-2009-0127853 A | 12/2009 |
| KR | 10-2014-0098566 A | 8/2014 |
| KR | 10-2016-0083610 A | 7/2016 |
| TW | 201334776 A1 | 9/2013 |
| WO | WO 2016/020724 A1 | 2/2016 |

OTHER PUBLICATIONS

Raskin et al. (2004) Current Pharmaceutical Design 10, 3419-3429. (Year: 2004).*
Revilla et al. (1998) J. Agric. Food Chem. 46: 4592-4597. (Year: 1998).*
Database WPI Week 201467, "Composition, useful as a nutraceutical composition for treating or preventing bone disease including osteoporosis and arthritis, comprises tsaoko fructus,"AN 2014-R75847, Sep. 24, 2014, 2 pages, XP002775390.
Extended European Search Report, dated Nov. 21, 2017, for European Application No. 17153322.7.
Jiang et al., "Li-Gan-Shi-Liu-Ba-Wei-San improves non-alcoholic fatty liver disease through enhancing lipid oxidation and alleviating oxidation stress.", J Ethnopharmacol., 2015, vol. 176, pp. 499-507.
Kim et al., "2,8-Decadiene-1, 10-Diol Inhibits Lipopolysaccharide-Induced Inflammatory Responses Through Inactivation of Mitogen-Activated Protein Kinase and Nuclear Factor-KB Signaling Pathway", Inflammation, 2015, vol. 39, No. 2, pp. 583-591.
Kim et al., "Nitric Oxide Inhibitory Constituents from the Fruits of Amomum tsao-ko." Natural Product Sciences, vol. 25, Issue 1, 2019, pp. 76-80.
Knier et al., "Neutralizing IL-17 protects the optic nerve from autoimmune pathology and prevents retinal nerve fiber layer atrophy during experimental autoimmune encephalomyelitis.", Journal of Autoimmunity, 2015, vol. 56, pp. 34-44.
Kostic et al., "IL-17 and Glutamate Excitotoxicity in the Pathogenesis of Multiple Sclerosis.", Scandinavian Journal of Immunology, 2014, vol. 79, pp. 181-186.
Lee et al., "Inhibitory Constituents of Lipopolysaccharide-Induced Nitric Oxide Production in BV2 Microglia isolated from Amomum tsao-ko," Planta Med., 2008, vol. 74, pp. 867-869.
Li et al., "Amomum tsao-ko Suppresses Lipopolysaccharide-Induced Inflammatory Responses in RAW264.7 Macrophages via Nrf2-Dependent Heme Oxygenase-1 Expression", Am. J. Chin. Med., 2014, vol. 42, No. 5, pp. 1229-1244.
Liu et ai., "Interleukin-17 (IL-17)-induced MicroRNA 873 (miR-873) Contributes to the Pathogenesis of Experimental Autoimmune Encephalomyelitis by Targeting A20 Ubiquitin-editing Enzyme.", Journal of Biological Chemistry, 2014, vol. 289, No. 42, pp. 28971-28986.
Luchtman et al., "IL-17 and related cytokines involved in the pathology and immunotherapy of multiple sclerosis: current and future developments.", Cytokine & Growth Factor Reviews, 2014, vol. 25, pp. 403-413.

(Continued)

Primary Examiner — Russell G Fiebig
(74) Attorney, Agent, or Firm — Birch, Stewart, Kolasch & Birch, LLP

(57) ABSTRACT

A method of treating or alleviating autoimmune-related diseases is provided. The method comprises administering a pharmaceutical composition to a subject in need thereof. Moreover, the pharmaceutical composition comprises an extract of Amomum tsao-ko as an effective ingredient and a pharmaceutically acceptable carrier or salt.

4 Claims, 16 Drawing Sheets

(56) References Cited

OTHER PUBLICATIONS

Makni et al., "Evaluation of the antioxidant, anti-inflammatory and hepatoprotective properties of vanillin in carbon tetrachloride-treated rats." European Journal of Pharmacology, vol. 668, 2011, pp. 133-139.

Niazi et al.. "Anti-inflammatory and antinociceptive activity of vanillin." Drug Development and Therapeutics, vol. 5, Issue 2, 2014, pp. 145-147.

Rahman et al., "Anti-quorum sensing and anti-biofilm activity of Amomum tsaoko (Amommum tsao-ko Crevost et Lemarie) on foodborne pathogens." Saudi J. Biol. Sci., vol. 24, 2017, pp. 324-330.

Raskin et al., "Can an apple a day keep the doctor away?" Current Pharmaceutical Design, vol. 10, 2004, pp. 3419-3429.

Revilla et al., "Comparison of several procedures used for the extraction of anthocyanins from red grapes." Journal of Agricultural and Food Chemistry, vol. 46, 1998, pp. 4592-4597.

Shin et al., "Amomum tsao-ko fruit extract suppresses lipopolysaccharide-induced inducible nitric oxide synthase by inducing heme oxygenase-1 in macrophages and in septic mice," International Journal of Experimental Pathology, 2016, vol. 96, pp. 395-405.

Taiwanese Office Action and Search Report, dated Jun. 28, 2017, for Taiwanese Application No. 106103204.

Yang et al., "Inhibition of Interferon Regulatory Factor 4 Suppresses Th1 and Th17 Cell Differentiation and Ameliorates Experimental Autoimmune Encephalomyelitis.", Scandinavian Journal of Immunology, 2015, pp. 345-351.

Zhang et al., "Anticomplementary principles of a Chinese multiherb remedy for the treatment and prevention of SARS.", J. Ethnopharmacol., 2008, vol. 117, pp. 351-361.

Zhang et al., "Bioactivity evaluation of ingredients identified from the fruits of Amomum tsaoko Crevost et Lemaire, a Chinese spice," Food & Function, vol. 5, No. 8, May 6, 2014, pp. 1747-1754.

* cited by examiner

METHOD FOR TREATING OR ALLEVIATING AUTOIMMUNE-RELATED DISEASES

CROSS REFERENCE TO RELATED APPLICATION

This application is a Divisional of pending U.S. patent application Ser. No. 15/416,304, filed on Jan. 26, 2017 and entitled "PHARMACEUTICAL COMPOSITION FOR TREATING OR ALLEVIATING AUTOIMMUNE-RELATED DISEASES AND METHOD FOR TREATING OR ALLEVIATING AUTOIMMUNE-RELATED DISEASES" which claims the benefit of provisional Application No. 62/287,345, filed on Jan. 26, 2016. The entirety of the above-mentioned patent applications are hereby incorporated by reference herein and made a part of this specification.

TECHNICAL FIELD

The technical field relates to pharmaceutical compositions for treating or alleviating autoimmune-related diseases.

BACKGROUND

Under a normal physiological condition, immune system can be regarded as the defense army of the body. When immune system detects the invasion of bacteria, virus, or other foreign materials, it will produce antibodies and attack these foreign materials. However, when immune system is disorder and no longer be able to accurately distinguish between the enemy and the self, the defense army will attack their own tissues or organs, and trigger the so-called "Autoimmune disease".

The prevalence of suffering from autoimmune disease is about 5% of the global population. The type of autoimmune disease ranges from single organ disease (such as Hashimoto's thyroiditis) to systemic diseases (such as systemic lupus erythematosus, referred to SLE). The pathological features of autoimmune disease include that a large number of abnormal infiltration lymphocytes can be found in the inflammatory tissues or organs, and the autoantibody can be detected in the blood of the patient.

In addition, the specific autoimmune diseases are regionally distributed and may be related to race, gene and environment. In the case of multiple sclerosis (MS), it usually occurs in the ancestors of the Caucasian race from Northern Europe, and the residents of high latitudes are more likely to suffer from MS. The current study shows that MS is a chronic inflammatory disease caused by auto-demyelination in central nerve system, and due to the damaged nerve is different, the clinical lesions of individual patient are different, including loss of balance, spasm, difficulty in hands and feet, paralysis, blurred vision and other symptoms.

Regarding the pathogenic mechanism of autoimmune diseases, many studies have pointed that overexpression of interferon or tumor necrosis factor may result in rheumatoid arthritis, Crohn's disease, psoriasis arthritis, and other immune-related diseases. Recent studies have shown that interleukin, such as IL-17, regulated by T helper cells, is also an important cytokine for dominating autoimmune reaction.

In the past, the main drugs used to treat autoimmune diseases include non-steroidal anti-inflammatory drugs, steroids, immune-modulators, and immune-suppressive agents. However, these drugs are known to have the risk of side effects, and somehow they may interact with each other.

In view of this, the new generation of therapeutic drugs are developed to adopt immuno-target therapy, which designs biological agents targeting for specific immune messages or molecules in autoimmune diseases, and these biological agents can accurately target abnormal immune molecules, but will not hurt the normal cells.

Therefore, there is an urgent demand to develop a low side-effect and specific biological agents at present.

SUMMARY

The disclosure provides a pharmaceutical composition for treating or alleviating autoimmune-related diseases, comprising: an extract of Amomum tsao-ko as an effective ingredient and a pharmaceutically acceptable carrier or salt.

The disclosure also provides a pharmaceutical composition for treating or alleviating autoimmune-related diseases, comprising: a compound as an effective ingredient and a pharmaceutically acceptable carrier or salt, wherein the compound is vanillin, tsaokoin, or a combination thereof.

The disclosure also provides a method of treating or alleviating autoimmune-related diseases, comprising: administering a pharmaceutical composition to a subject in need thereof, wherein the pharmaceutical composition comprises an extract of Amomum tsao-ko as an effective ingredient and a pharmaceutically acceptable carrier or salt.

Furthermore, the disclosure provides a method of treating or alleviating autoimmune-related diseases, comprising: administering a pharmaceutical composition to a subject in need thereof, wherein the pharmaceutical composition comprises a compound as an effective ingredient and a pharmaceutically acceptable carrier or salt, wherein the compound is vanillin, tsaokoin, or a combination thereof.

The present disclosure can be more fully understood by reading the subsequent detailed description and exemplary embodiments with references to the accompanying drawings so as to be easily realized by a person having ordinary knowledge in the art, wherein:

DETAILED DESCRIPTION

Figure 1:
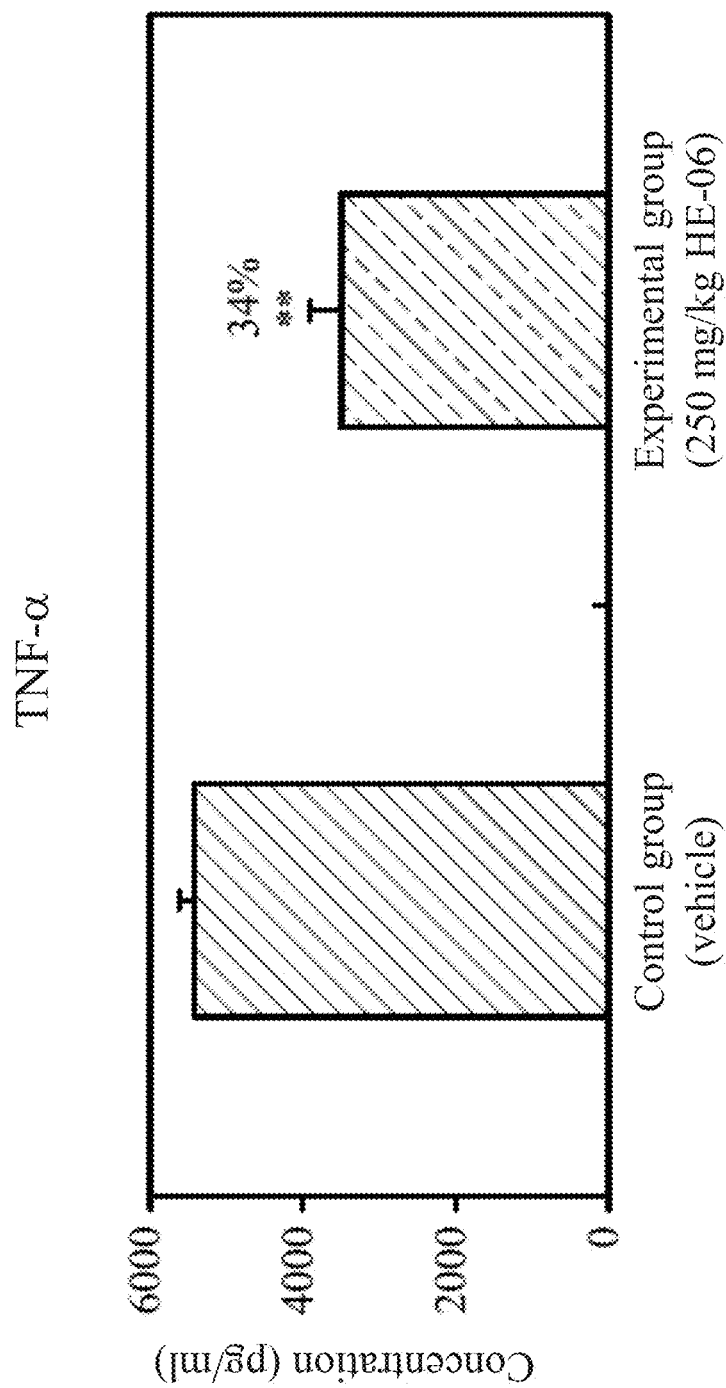
FIG. 1 shows the effect of Amomum tsao-ko extract HE-06 on TNF-α secretion in LPS-induced acute inflammatory BALB/c mouse model. ** represents p value is less than 0.01.

In the following detailed description, for purposes of explanation, numerous specific details are set forth in order to provide a thorough understanding of the disclosed embodiments. It will be apparent, however, that one or more embodiments may be practiced without these specific details. In other instances, well-known structures and devices are schematically shown in order to simplify the drawing.

The disclosure provides a pharmaceutical composition for treating or alleviating autoimmune-related diseases, which comprises an effective amount of an extract of Amomum tsao-ko (hereinafter referred to as A. tsao-ko) as a main effective ingredient and a pharmaceutically acceptable carrier or salt. The above-mentioned A. tsao-ko is belong to evergreen perennial herb of Zingiberaceae cardamom genus, with a height of 2.5 to 3 meters and grown in forest humid zone of tropical and subtropical. Otherwise, the origin of A. tsao-ko is distributed in Yunnan of China and Southeast Asia, and its artificial cultivation history has been 200 years. In addition to herbal medicine, the dry fruit of A. tsao-ko can also be used as seasonings because of its whole plant having spicy flavor. Hence, A. tsao-ko can be considered as both food and medicine material.

The above-mentioned extract of A. tsao-ko is extracted from the root, stem, leaf, flower, fruit, seed, bark or a combination thereof. In one embodiment, the above-mentioned extract of A. tsao-ko can be extracted from the fruit of A. tsao-ko.

The above-mentioned extract of A. tsao-ko is obtained from performing an extraction with an organic solvent. The said organic solvent may comprise alcohol, ester, alkane, haloalkane, or a combination thereof, but it is not limited thereto.

The above-mentioned alcohol may be C1-C12 alcohols (for example, methanol, ethanol, propanol, isopropanol, n-butanol, 2-butanol, t-butanol, 1,3-butanediol, 1,4-butanediol, pentanol, isoamyl alcohol, 2,3-pentanediol, 2,4-pentanediol, cyclopentanol, hexanol, cyclohexanol, heptanol, octanol, nonanol, decanol, hendecanol, dodecanol, etc.), the above-mentioned esters may be C2-O5 acid esters (for example, ethyl acetate, propyl acetate, amyl acetate, amyl propionate, etc.), the above-mentioned alkanes may be C5-C6 alkanes (for example, n-heptane, n-pentane, cyclopentane, n-hexane, cyclohexane, etc.), and the above-mentioned haloalkane may be, for example, methyl chloride or ethyl chloride, but it is not limited thereto.

In one embodiment, the above-mentioned extract of A. tsao-ko can be obtained from performing an extraction with alcohol solvent. In another embodiment, the extract of A. tsao-ko can be obtained from performing an extraction by alcohol solvent with the concentration of ranging from 50 to 95%. In which, the concentration of the alcohol solvent utilized to perform the extraction of A. tsao-ko can be 50-60%, 60-70%, 70-80%, 80-90%, or 90-95%. In another embodiment, the concentration of the alcohol solvent utilized to perform the extraction of A. tsao-ko can be 95% alcohol solvent.

Before extraction, the weight of A. tsao-ko which would be used this time is calculated first, and the extraction is then carried out by the proportion of which a volume of the organic solvent is 3-10 times the weight of A. tsao-ko. In one embodiment, the volume of the organic solvent can be 3-7 times the weight of A. tsao-ko. In another embodiment, the volume of the organic solvent can be 5 times the weight of A. tsao-ko. In addition, the extraction is performed an extraction temperature of 10 to 35° C. and an extraction time of 3 to 10 days. In one embodiment, the extraction temperature can be 20 to 30° C. and the extraction time can be 5 to 8 days. In another embodiment, the extraction temperature can be 25° C. and the extraction time can be 7 days.

In one embodiment, the extraction of the extract of A. tsao-ko is further performed with a shaking mode, including horizontal shaking, vertical shaking, rotate shaking, 3D-nutating shaking, seesaw shaking, ultrasonic shaking or a combination thereof, but it is not limited thereto. The extract of A. tsao-ko obtained by the preceding extraction process is still passed through a suction filtration step and the resulting filtrate is considered as the test substance of the extract of A. tsao-ko, hereinafter referred to as HE-06.

In one embodiment, the extraction of the above-mentioned extract of A. tsao-ko HE-06 further comprises a distillation step. In another embodiment, the extraction of the above-mentioned extract of A. tsao-ko HE-06 still comprises a heating reflux step with a low polarity solvent.

Otherwise, in one embodiment, the pharmaceutical composition comprising the above-mentioned extract of A. tsao-ko HE-06 as an effective ingredient has the effect on inhibiting cytokine secretion, and the said cytokine includes IL-17, TNF-α, and a combination thereof, but it is not limited thereto.

In another embodiment, the pharmaceutical composition comprising the above-mentioned extract of A. tsao-ko HE-06 as an active ingredient can be used for treating or alleviating autoimmune-related diseases. The said treating or alleviating autoimmune-related diseases can include, but is not limited to, alleviating the syndrome of the autoimmune-related diseases or slowing down the progress of the autoimmune-related diseases. In which, the said autoimmune-related diseases can include Multiple Sclerosis (MS), neuromyelitis optica (NMO), acute disseminated encephalomyelitis (ADEM), demyelination-related neuritis, Ankylosing spondylitis, Psoriasis, Psoriatic arthritis, Rheumatoid arthritis (RA), Crohn's disease, Juvenile idiopathic arthritis (JIA), Ulcerative Colitis (UC), and a combination thereof, but it is not limited thereto. In one embodiment, the pharmaceutical composition comprising the above-mentioned extract of A. tsao-ko HE-06 as an effective ingredient can be used for treating or alleviating Multiple Sclerosis.

In another embodiment, the pharmaceutical composition comprising the above-mentioned extract of A. tsao-ko HE-06 as an effective ingredient may be administered orally, non-orally, parenterally by an inhalation spray, or via an implanted reservoir. The parenteral method may comprise subcutaneous, intracutaneous, intravenous, intramuscular, intra-articular, intra-arterial, intrasynovial, intrasternal, intrathecal, and intralesional injection or infusion techniques, but it is not limited thereto.

An oral composition can comprise, but is not limited to, tablets, capsules, emulsions, aqueous suspensions, dispersions and solutions.

In one embodiment, the pharmaceutical composition can be administered by oral or subcutaneous injection. It is also possible to administer with multi-dose thereof in a suitable period according to the pharmacological routine method for determining the course of administration to which the patient is applied.

The pharmaceutical composition comprising the above-mentioned extract of A. tsao-ko HE-06 as an effective ingredient further comprises a pharmaceutically acceptable carrier or salt well known in the art and added in appropriate proportion. The pharmaceutically acceptable carrier may include, but is not limited to, a solvent, a dispersion medium, a coating, an antibacterial and antifungal agent, or an isotonic and absorption delaying agent, etc. which is compatible to pharmaceutical administration. The pharmaceutical composition can be formulated into dosage forms for different administration routes utilizing conventional methods.

Moreover, the pharmaceutically acceptable salt may include, but is not limited to, inorganic cation salt, such as alkali metal salts such as sodium salt, potassium salt or amine salt, such as alkaline-earth metal salt such as magnesium salt or calcium salt, such as the salt containing bivalent or quadrivalent cation such as zinc salt, aluminum salt or zirconium salt. In addition, the pharmaceutically acceptable salt may also comprise organic salt, such as dicyclohexylamine salt, methyl-D-glucamine, and amino acid salt such as arginine, lysine, histidine, or glutamine.

In one embodiment of the present disclosure, a method of treating or alleviating autoimmune-related diseases is also provided, in which the method comprises administering a pharmaceutical composition to a subject in need thereof, and the pharmaceutical composition comprises an extract of A. tsao-ko as an effective ingredient and a pharmaceutically acceptable carrier or salt. The said subject can include mammals, such as rat, dog, cat, horse, sheep, pig, monkey, ape, etc., especially human.

In another embodiment of the present disclosure, a pharmaceutical composition for treating or alleviating autoimmune-related diseases is provided, in which the pharmaceutical composition comprises a compound as an effective ingredient and a pharmaceutically acceptable carrier or salt, and the compound is vanillin, tsaokoin, or a combination thereof.

In which, the above-mentioned vanillin and tsaokoin are derived from the extract of A. tsao-ko, HE-06, which is obtained by performing the extraction with the proportion of organic solvent volume/A. tsao-ko weight=3-10/1, at 10-35° C. for 3 to 10 days shaking.

In one embodiment, the above-mentioned extract of A. tsao-ko, HE-06, is further extracted with a distillation step to remove the portion of essential oil. Then, a step of heating and refluxing with a low polarity solvent is performed to reduce the toxicity and extract the active ingredient therein. The said low polarity solvent can include petroleum ether, C4-C9 linear alkanes (such as n-Hexane), n-Heptane, C4-C9 cycloalkanes, unsaturated benzene, esters, ketones, and a combination thereof, but it is not limited thereto.

With regard to the extraction of the extract of A. tsao-ko, including the above-mentioned extraction site, the type, concentration and volume of the utilized organic solvent, the extraction condition employed in the extraction process including the extraction temperature, time, accompanied shaking mode, etc., as described in the above description, will not repeat them here.

In another embodiment, the pharmaceutical composition comprising vanillin, tsaokoin or a combination thereof as an effective ingredient has the effect on inhibiting cytokine secretion, and the cytokine includes IL-17, TNF-α, and a combination thereof, but it is not limited thereto.

In yet another embodiment, the pharmaceutical composition comprising vanillin, tsaokoin or a combination thereof as an effective ingredient can be can be used for treating or alleviating autoimmune-related diseases. The said treating or alleviating autoimmune-related diseases can include, but is not limited to, alleviating autoimmune-related diseases or slowing down autoimmune-related diseases. In which, the said autoimmune-related diseases can include Multiple Sclerosis (MS), neuromyelitis optica (NMO), acute disseminated encephalomyelitis (ADEM), demyelination-related neuritis, Ankylosing spondylitis, Psoriasis, Psoriatic arthritis, Rheumatoid arthritis (RA), Crohn's disease, Juvenile idiopathic arthritis (JIA), Ulcerative Colitis (UC), and a combination thereof, but it is not limited thereto. In one embodiment, the pharmaceutical composition comprising vanillin, tsaokoin or a combination thereof as an effective ingredient can be used for treating or alleviating Multiple Sclerosis.

In another embodiment, the pharmaceutical composition comprising vanillin, tsaokoin or a combination thereof as an effective ingredient may be administered orally, non-orally, parenterally by an inhalation spray, or via an implanted reservoir. With regard to the form of oral or non-oral administration, and the medication administration, as described in the above description, will not repeat them here.

In addition, the pharmaceutical composition comprising vanillin, tsaokoin or a combination thereof as an effective ingredient further comprises a pharmaceutically acceptable carrier or salt well known in the art and added in appropriate proportion. With regard to the species of pharmaceutically acceptable carrier or salt, as described in the above description, will not repeat them here.

Hence, in another embodiment of the present disclosure, a method of treating or alleviating autoimmune-related diseases is provided, in which the method comprises administering a pharmaceutical composition to a subject in need thereof, wherein the pharmaceutical composition comprises a compound as an effective ingredient and a pharmaceutically acceptable carrier or salt, wherein the compound is vanillin, tsaokoin, or a combination thereof. With regard to the subject to which is administered, as described in the above description, will not repeat them here.

EXAMPLES

The specific embodiments of the present disclosure are described as follows. However, the following examples are merely illustrative of the technical aspects of the present invention and should not be construed as limiting the scope of the invention.

Example 1: Preparation of the Extract of A. Tsao-Ko HE-06

A. Material

The fruit of A. tsao-ko was taken as the medicinal material. After cleaning and drying, the fruit of A. tsao-ko was initially crushed by herbs crusher.

B. Method

About 500 g of the crude crushed of A. tsao-ko was immersed in 5-fold volume (about 2500 mL) of 95% ethanol at 25° C. with shaking of 125 rpm in shaker for 7 days. The extract was then collected for suction filtration. Thereafter, the filtered filtrate was quantified and sampled 2 mL for analysis by high performance liquid chromatography (HPLC) and thin film chromatography (TLC). The remaining filtrate was concentrated under reduced pressure to a volume of about 30 mL, which was then dispensed and freeze-dried to be the test substance of the extract of A. tsao-ko, hereinafter referred to as HE-06.

Example 2: The Extract of A. Tsao-Ko HE-06 can Inhibit IL-17 Secretion

A. Anti-IL-17 Secretion in EL4 (Murine Lymphoma) Cells (1) Cell Culture

EL4 cell line is murine lymphoma cell purchased from Bioresource Collection and Research Center (referred to as BCRC) and cultured in RPMI 1640 medium which contains 10% Fetal Bovine Serum (referred to as FBS), 1.5 g Sodium bicarbonate, 1 mM Sodium pyruvate, lx non-essential amino acids (referred to as NEAA), and 0.5 mM 2-Mecaptoethanol (referred to as 2-ME). The subculture was performed 2-3 times a week and the culture condition was according to the suggestion of BCRC.

(2) IL-17 Secretion and MTT Test

EL4 lymphoma cells were seeded into 96-well plate by $1 \times 10^5$ cells per well and 10 µl of the extract of A. tsao-ko HE-06 was added to each well and incubated at 37° C. in 5% $CO_2$ cell incubator for 1 hour. Then, Phorbol-12-myristate-13-acetate (referred to as PMA or TPA) and Ionomycin were added to be the stimulants that induce activation of lymphoma cells, in which the final concentration of PMA was 10 ng/ml and the final concentration of Ionomycin was 5 ng/ml, and additional 18 hours incubation was executed. In the above test, the group of adding both PMA (final concentration of 10 ng/ml) and Ionomycin (final concentration of 5 ng/ml) was considered as the control group.

Thereafter, the cell-containing 96-well plate was centrifuged at 1200 rpm for 5 minutes and the supernatant was collected and transferred to the new 96-well plate. 5 µl MTT of 5 mg/ml was added to the cells in original 96-well plate and 1 hour incubation of 37° C. and 5% $CO_2$ in cell incubator was executed to generate crystal violet. 150 µl DMSO was then added to dissolve the crystal violet and the absorbance of 570 nm was measured to assess the cell viability.

As for the supernatant in new 96-well plate, mouse IL-17 ELISA kit (R&D, DY421E) was used to detect the IL-17 secretion, and the foregoing IL-17 amount in supernatant represents the IL-17 amount secreted by the cells. In addition, the detection results of IL-17 secretion were first normalized by the control group as 100%, and $IC_{50}$ of the extract of A. tsao-ko HE-06 on inhibiting IL-17 secretion was calculated. The results were shown in Table 1.

B. Anti-IL-17 Secretion in Rat PBL (Peripheral Blood Leukocyte) (1) Cell Culture The blood of SD rats (Sprague Dawley rat) was collected by means of sapheneous vein sampling and then placed in EDTA-containing centrifuge tubes (the final concentration of EDTA was 2 mg/ml) as well as mixed homogeneously. Then about 4-fold the total volume of blood and EDTA of red blood cell lysate (ACK Lysis Buffer or Red Blood Cell Lysis Buffer) was added to break the red blood cells. The reaction was carried out at 37° C. water bath for 5 minutes, and then about 4-fold the total volume of blood, EDTA and erythrocyte lysate of buffer (PBS buffer) was added and the supernatant was removed by centrifugation at 3000 rpm for 5 minutes. The foregoing step of breaking the red blood cells was repeated twice, and then centrifugation was performed to obtain the precipitated part, namely PBL. Thereafter the appropriate volume of RPMI cell culture medium was added for culture.

(2) Test of Inhibition in IL-17 Secretion

PBL cells were seeded into 96-well plate by $2 \times 10^5$ cells per well and 10 µl of the extract of A. tsao-ko HE-06 was added to each well and incubated in 37° C. and 5% $CO_2$ cell incubator for 1 hour. Then, (final concentration of 10 ng/ml) and Ionomycin (final concentration of 5 ng/ml) were added to be the stimulants that induce activation of lymphoma cells, and additional 48 hours incubation was executed. In the above test, the group of adding both PMA (final concentration of 10 ng/ml) and Ionomycin (final concentration of 5 ng/ml) was considered as the control group.

Thereafter, the cell-containing 96-well plate was centrifuged at 3000 rpm for 5 minutes and the supernatant was collected and transferred to the new 96-well plate. 5 µl AlamarBlue was added to the cells in original 96-well plate and additional 4 hours incubation of 37° C. and 5% $CO_2$ in cell incubator was executed. Then, the cell viability was assessed by ELISA reader to measure the absorbance of excitation light at 560 nm as well as the emitting light at 590 nm.

As for the supernatant in new 96-well plate, rat IL-17 ELISA kit (eBioscience, 88-7170) was used to detect the IL-17 secretion. In addition, the detection results of IL-17 secretion were first normalized by the control group as 100%, and $IC_{50}$ of the extract of A. tsao-ko HE-06 on inhibiting IL-17 secretion was calculated. The results were also shown in Table 1.

TABLE 1

The inhibitory effects of HE-06 on IL-17 secretion in EL4 murine lymphoma cells and rat Peripheral Blood Leukocytes. $IC_{50}$ is the HE-06 concentration causing 50% IL-17 secretion inhibition.

| Test sample | $IC_{50}$ (µg/ml) | |
| --- | --- | --- |
| | EL4 | PBL |
| HE-06 | 27.9 | 9.9 |

The results of in vitro cell analysis shown in Table 1 indicated that the extract of A. tsao-ko HE-06 can inhibit the secretion of IL-17 in PMA and Ionomycin-induced EL4 lymphoma cells and peripheral blood leukocytes.

Example 3: The Extract of A. Tsao-Ko HE-06 can Inhibit TNF-α Secretion (1) Experimental Animal The 6-8 weeks BALB/c male mice were purchased from BioLASCO Taiwan Co., Ltd. In addition to make the feeding condition meeting with national experimental animal guidelines, the batch of mice were marked, sub-cage and weighing soon after acquisition. Then, these mice were placed to the quarantine room of general area for a week of quarantine work. During the quarantine period, observation of mobility and environmental adaptability was performed, and after assessment to be normal, these mice were transferred into the feeding area for experimental implementation.

The light of feeding area was auto-controlled by 12 hours light and 12 hours dark, as well as the room temperature was controlled at 23±2° C. During feeding, mice were free to obtain adequate food and drinking water. Due to abundant basic references and related data have been established for this laboratory animal strain, it is applicable to inflammatory functional assessment test. The experimental methods established in the following inflammatory models have been approved by the IACUC Committee of ITRI.

(2) Establish the Model of Acute Inflammation in Mice

Before the experiment, the mice were weighed and grouped so that the average body weight of each group was not significantly different. Then the mice were fasted for 2 to 4 hours but regular drinking water was still supplied. LPS stimulation, and the control group was given the same volume of solvent. After administration, the clinical symptoms of the mice were observed and recorded. Thereafter, LPS stimulation (about 0.25 ml/mouse) was conducted by IP injection. In which, the mice in experimental group were administered orally with the extract of A. tsao-ko HE-06 2 hours before LPS stimulation, and the mice in control group were administered with the same volume of solvent. After administration, the clinical symptoms of the mice were observed and recorded.

After 1.5 hours LPS stimulation, the mice were euthanized by excessive $CO_2$ and the whole blood was collected by cardiac puncture blood sampling. Next, the plasma was collected after centrifugation at 6000 rpm and 4° C. for 10 minutes and then TNF-α secretion were analyzed.

(3) Detection and Analysis of TNF-α Secretion

The TNF-α secretion in plasma was analyzed according to the following procedure shown in Duoset® ELISA kit. First, 100 µl of the Capture Antibody mixture solution was added to each well of the 96-well plate at room temperature to cover the surface of each well overnight. After that, their mixture solution was dried and washed with 300 µl Wash Buffer per well three times. Next, 200 µl of Block buffer was added at room temperature for 1 hour, and the previous wash step was repeated. Thereafter, 100 µl test sample (the foregoing plasma) and standard of appropriate dilution were added to each well to stand at room temperature for 2 hours, and the aforementioned washing step was repeated. Then, 100 µl of Detection Antibody mixture solution was added to each well to stand at room temperature for 2 hours, and the aforementioned washing step was repeated again. Thereafter, 100 µl of Streptavidin-HRP mixture solution was added to each well for reaction at room temperature away from light for 20 minutes. After repeating the aforementioned washing step, 100 µl of Substrate Solution (TMB) was added to each well for reaction at room temperature away from light for 20 minutes. Finally, 50 µl of Stop Solution (1N HCl) was added to each well to stop the color reaction, and the absorbance of $OD_{450}$ nm was measured.

The experimental results were expressed by mean±standard error (referred to as S.E.), and t-test statistics was used to distinguish the differences between the groups. ** represents that p value of less than 0.01 and indicates that there exists a statistically significant difference between the two groups. The experimental results are shown in FIG. 1.

As shown in FIG. 1, the extract of A. tsao-ko HE-06 could inhibit the secretion of TNF-α in LPS-induced acute inflammatory mice, and the inhibition level was up to 34%, indicating that the extract of A. tsao-ko HE-06 could effectively in vivo inhibit TNF-α secretion induced by inflammation.

Example 4: The Extract of A. Tsao-Ko HE-06 can Slow Down the progress of Experimental autoimmune encephalomyelitis (EAE) and improve the clinical symptoms of EAE (1) Experimental Animal The experimental animals, female C57BL/6 mice, aged about 8 weeks, were purchased from National Laboratory Animal Center (Tainan). After acclimation and quarantine, the mice were approximately 10-12 weeks of age at the time of performing the EAE experiments. The experimental animals were bred in the environment: 12 hours light and 12 hours dark, room temperature of 23±2° C., and relative humidity of 40-70%. During feeding, animals were free to obtain adequate food and drinking water, but after the onset of EAE, the soaked soft feed and agar gel jelly were especially given in the bottom of the feeding cage, so that the onset animals were easier to feed and drink. In addition, during the quarantine and testing period, the animals were observed and recorded by the veterinarian and the experimental staff of ITRI to ensure health of these experimental animals.

(2) Establishment of Autoimmune Mouse Model of EAE

The foregoing C57BL/6 mice were administered subcutaneously with 200 µl emulsion including 200 µg MOG35-55 peptide and 400 µg *Mycobacterium tuberculosis* H37Ra, followed by intraperitoneal injection of 500 ng pertussis toxin for induction of EAE. From the $7^{th}$ day after induction, the EAE clinical symptoms were recorded daily according to the recognized Ataxia score (grading of nervous system disorder) and EAE score as the scoring criteria (description of Ataxia score and EAE score are as follows). When the experimental animals began to appear Ataxia score 0++, followed by S-type grouping, and began to administrate the extract of A. tsao-ko HE-06 for 14 days. During the period, the condition of the mice was observed daily and their clinical symptoms were recorded according to the EAE score, and the group only administered with solvent was considered as the control group. Thereafter, animals were sacrificed on the $15^{th}$ day, and blood or related organs were collected for subsequent analysis.

(3) Records and Data Analysis of Ataxia Score and EAE Score

The criteria of Ataxia score are as follows: 0+ represents that the rear foot of the animal is splayed while moving, swing left and right, and gait imbalance; 0++ represents that when grasping the rear neck of the animal to observe whether its tail can be raised by itself and to test the tensile strength of its tail by fingers, the tail appears unable to be raised by itself as well as reduced tension.

The criteria of EAE score are as follows: Score 0 represents no EAE symptoms; Score 0.5 represents temporal weak tail, sometimes raised; Score 1 represents limp tail, unable to lift normally; Score 2 represents paralyzed tail or slightly hind limb weakness; Score 3 represents moderate to severe hind limb paralysis or mild forelimb weakness; Score 4 represents complete hind limb paralysis or moderate to severe forelimb weakness; Score 5 represents limb paralysis accompanied by incontinence or presenting a dying state; Score 6 represents death.

Figure 2A:
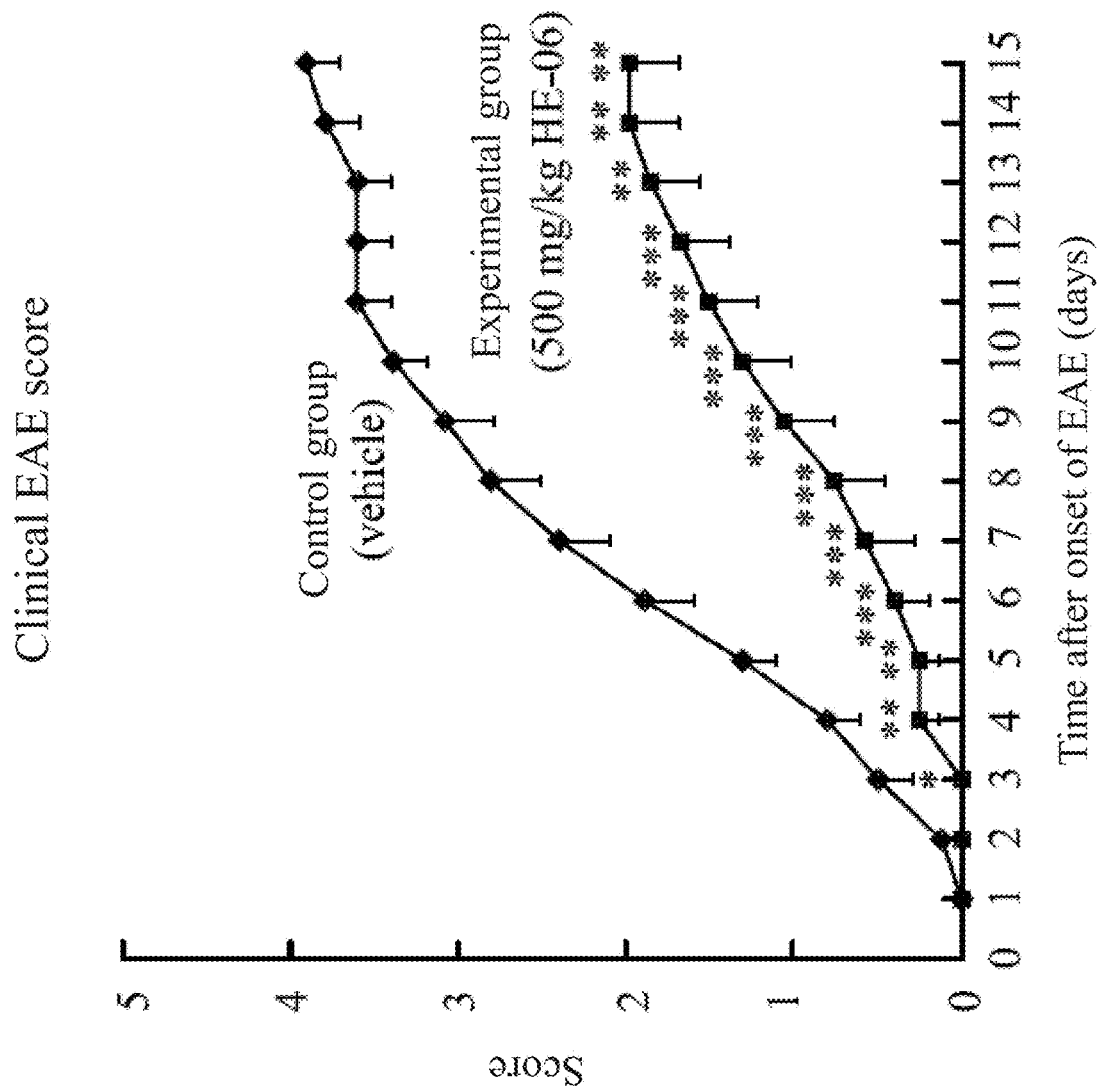
FIG. 2A shows that Amomum tsao-ko extract HE-06 exhibits the effect on delaying the progression of experimental autoimmune encephalomyelitis (EAE) in C57BL/6 mouse model, in which the results were obtained through daily observation and recording for 14 consecutive days, and the scoring criteria of the progression is based on Ataxia score and EAE score which have been recognized in literature. * represents p value is less than 0.05;  represents p value is less than 0.01; * represents p value is less than 0.001.

The experimental results were expressed by mean±standard error of mean (referred to as S.E.M.), and t-test statistics was used to distinguish the differences between the groups. In which * represents p value of less than 0.05;  represents p value of less than 0.01; * represents p value of less than 0.001 and these asterisk indicate that there exists a statistically significant difference between the two groups. The experimental results are shown in FIG. 2A.

As shown in FIG. 2, after induction of EAE, the mice have been to show the clinical symptoms of hind limb paralysis and severe forelimb weakness (such as Score 4 described above) on $14^{th}$ day after onset, but administering the extract of A. tsao-ko HE-06 could significantly slow down the progress of EAE, indicating that the extract of A. tsao-ko HE-06 could effectively improve the clinical symptoms in EAE animal model.

Example 5: Purification, Preparation and Toxicity-Attenuation Test of the Active Fractional Interval (I) of HE-06

The extract of A. tsao-ko, HE-06 was further extracted with a distillation step by steam for 24 hours to remove the portion of essential oil. Then, a step of heating and refluxing with a specific solvent was performed for 8 hours to remove the dregs and reduce the toxic portion.

Figure 2B:
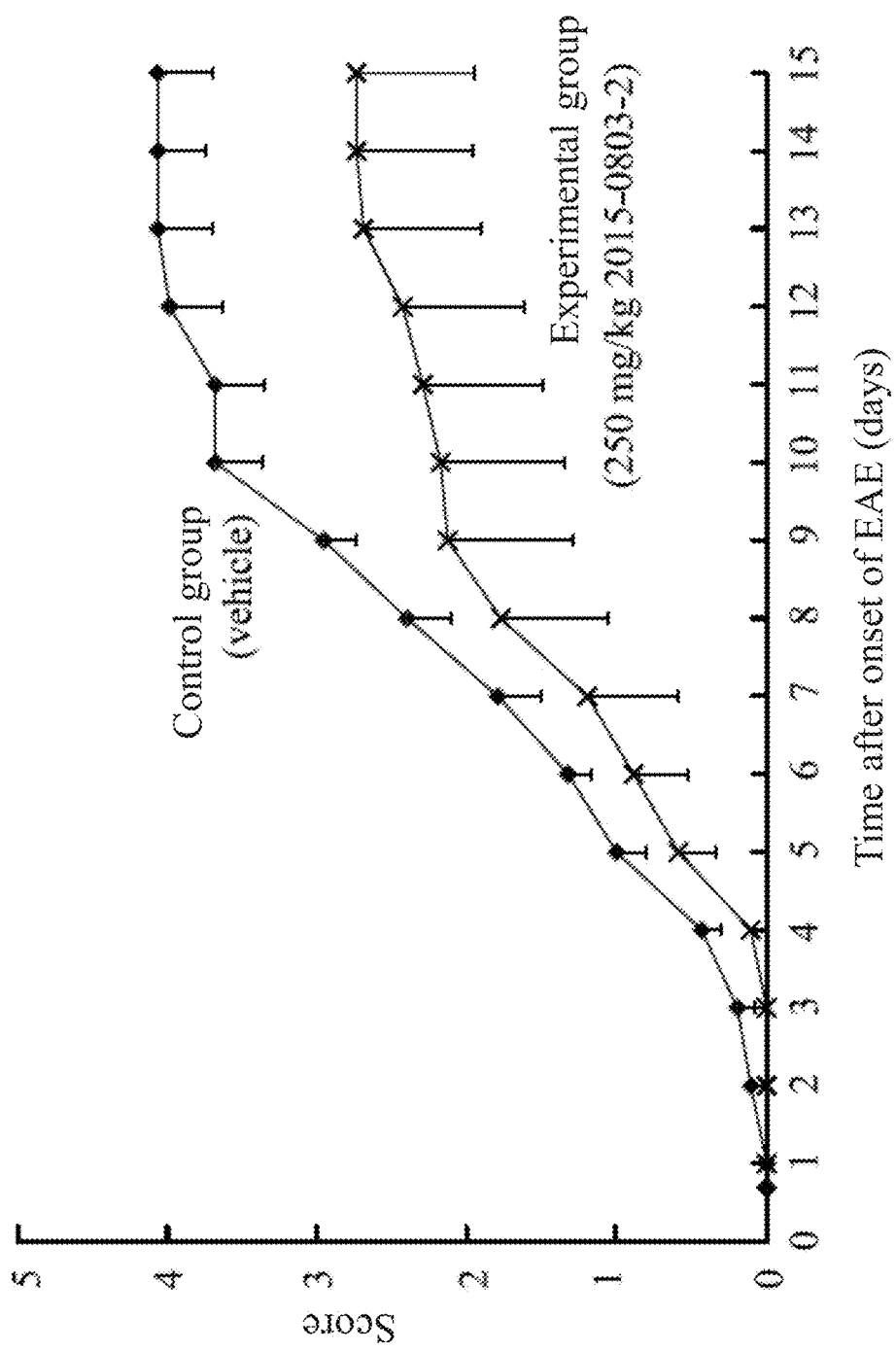
FIG. 2B-2C show the effects of the extracts, 2015-0803-2 and 2015-0909-2, on the progression of EAE mouse model, respectively. In which 2015-0803-2 and 2015-0909-2 are the further extracts of Amomum tsao-ko extract HE-06 and obtained through the toxicity-attenuating steps, and both 2015-0803-2 and 2015-0909-2 extracts are administered with a dose of 250 mg/kg. In which  represents p value is less than 0.01; * represents p value is less than 0.001.

With regard to the step of reducing the toxic portion, if the solvent {n-Hexane Ethyl acetate=1:1} was utilized to perform the step of heating and refluxing for 8 hours, the resulting extract was designated as 2015-0803-2. Further, by EAE mouse model test, the results indicated that although the clinical symptoms of the ten EAE mice administered with 2015-0803-2 of 250 mg/kg have been improved (as shown in FIG. 2B), still three mice were resulted to death.

Figure 2C:
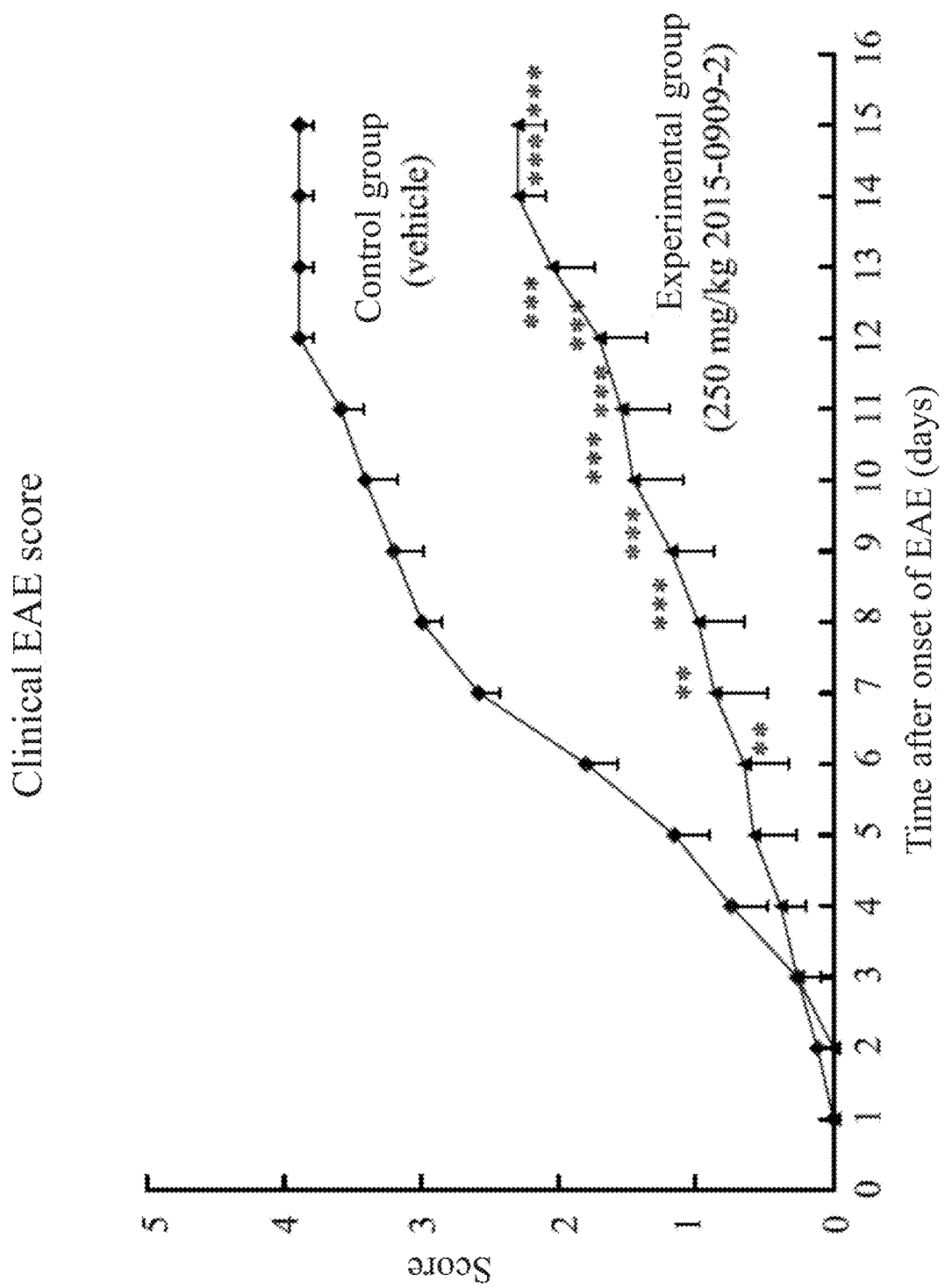

However, if the solvent was replaced with the low polarity solvent n-Hexane to perform the step of heating and refluxing for 8 hours, and then the extract was eluted by gradient elution with n-Hexane, EtOAc and MeOH (i.e., the solvent with lower polarity is utilized to separate the material which is easily eluted, and then the amount of solvent with higher polarity is gradually increased, so that the closely adsorbed material can be removed from the column), and the step of Silica Gel Column Chromatography was further performed. Each fractional interval was assessed via the cell activity test and the optimal active fractional interval was obtained, in which the extract was designated as 2015-0909-2. In the Same way, by EAE mouse model test, the results indicated that the clinical symptoms of the ten EAE mice administered with 2015-0909-2 of 250 mg/kg have been improved (as shown in FIG. 2C) and none mice were resulted to death. In which * represents p value of less than 0.05;  represents p value of less than 0.01; * represents p value of less than 0.001.

Hence, the extract 2015-0909-2 with the better toxicity-attenuating effect was considered as the active fractional interval (I) of HE-06.

Example 6: The Active Fractional Interval (I) of HE-06 can Improve the Clinical Symptoms of EAE Except for the drugs to be administered was replaced with the active fractional interval (I) of HE-06 and the administered active fractional interval (I) of HE-06 with the concentration of 0 mg/kg (as the control group or vehicle), 30 mg/kg, and 100 mg/kg, the experimental animals, the established of mouse autoimmune EAE model, and the scoring criteria are the same as described above, and will not repeat them here. The experimental results were shown in FIG. 3A-3E. In which the group administered with solvent of the equal volume was considered as the control group, and the group administered with 5 mg/kg methylprednisolone (a steroid medication, can be used for anti-inflammation) was considered as the positive control group.

Figure 3A:
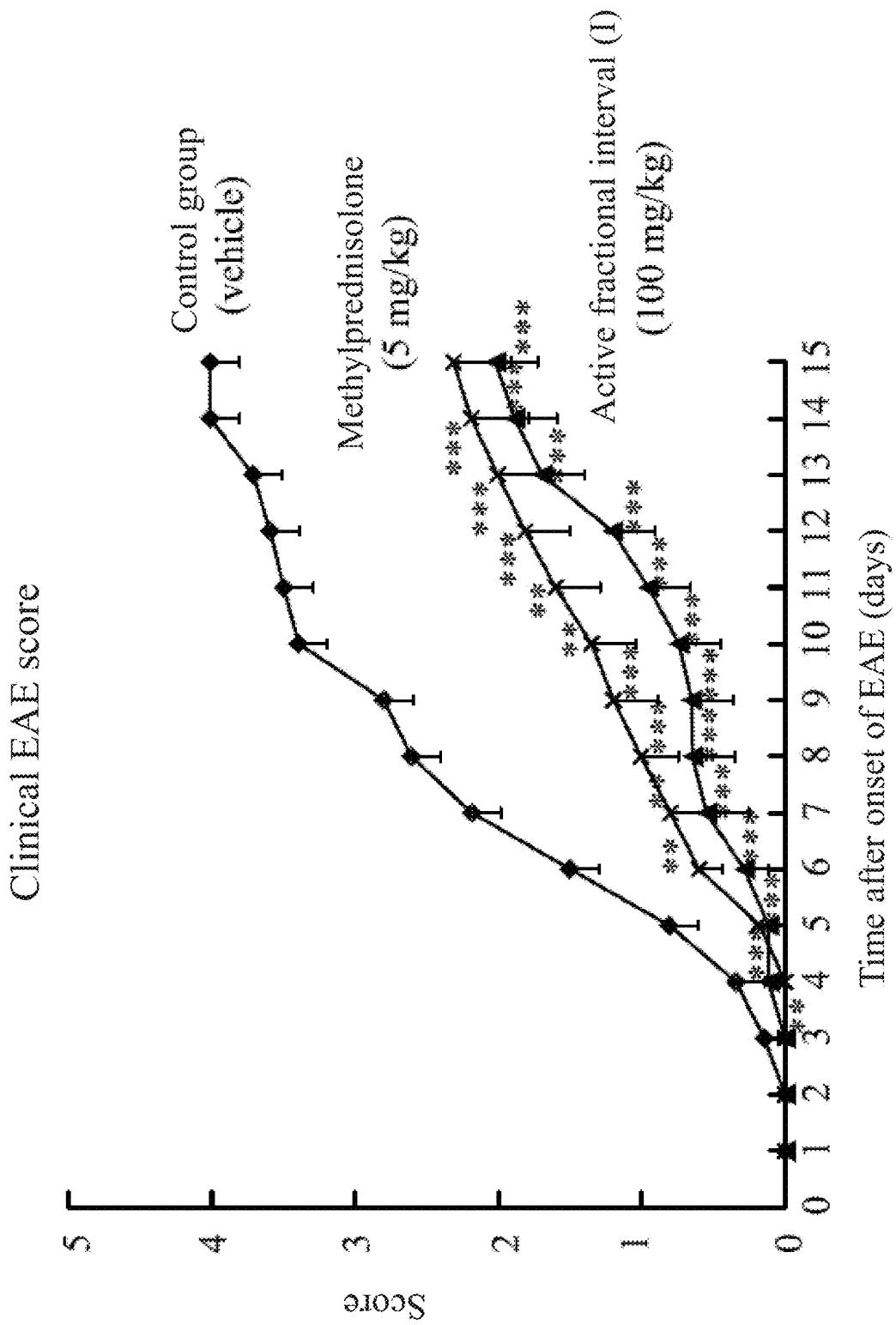
FIG. 3A-3E show the effects of active fractional interval (I) of Amomum tsao-ko extract HE-06 on EAE acute inflammatory mouse model, including delaying the development of EAE progression, improving EAE disorders, improving demyelination of the cervical spine, and reducing the incidence of demyelination and axonal swelling in the entire spinal cord, respectively. In which * represents p value is less than 0.05;  represents p value is less than 0.01; * represents p value is less than 0.001.
Figure 3B:
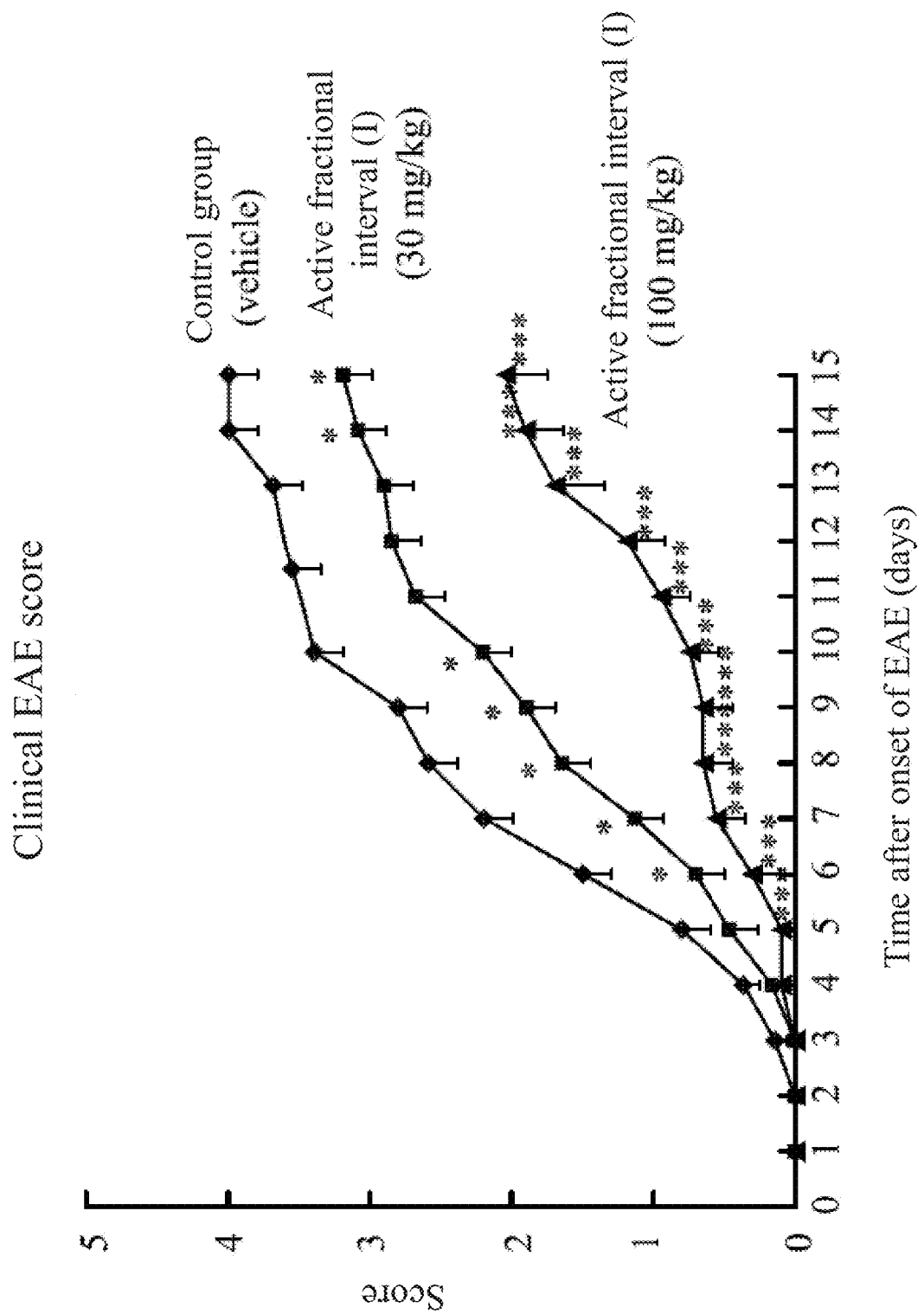
Figure 3C:
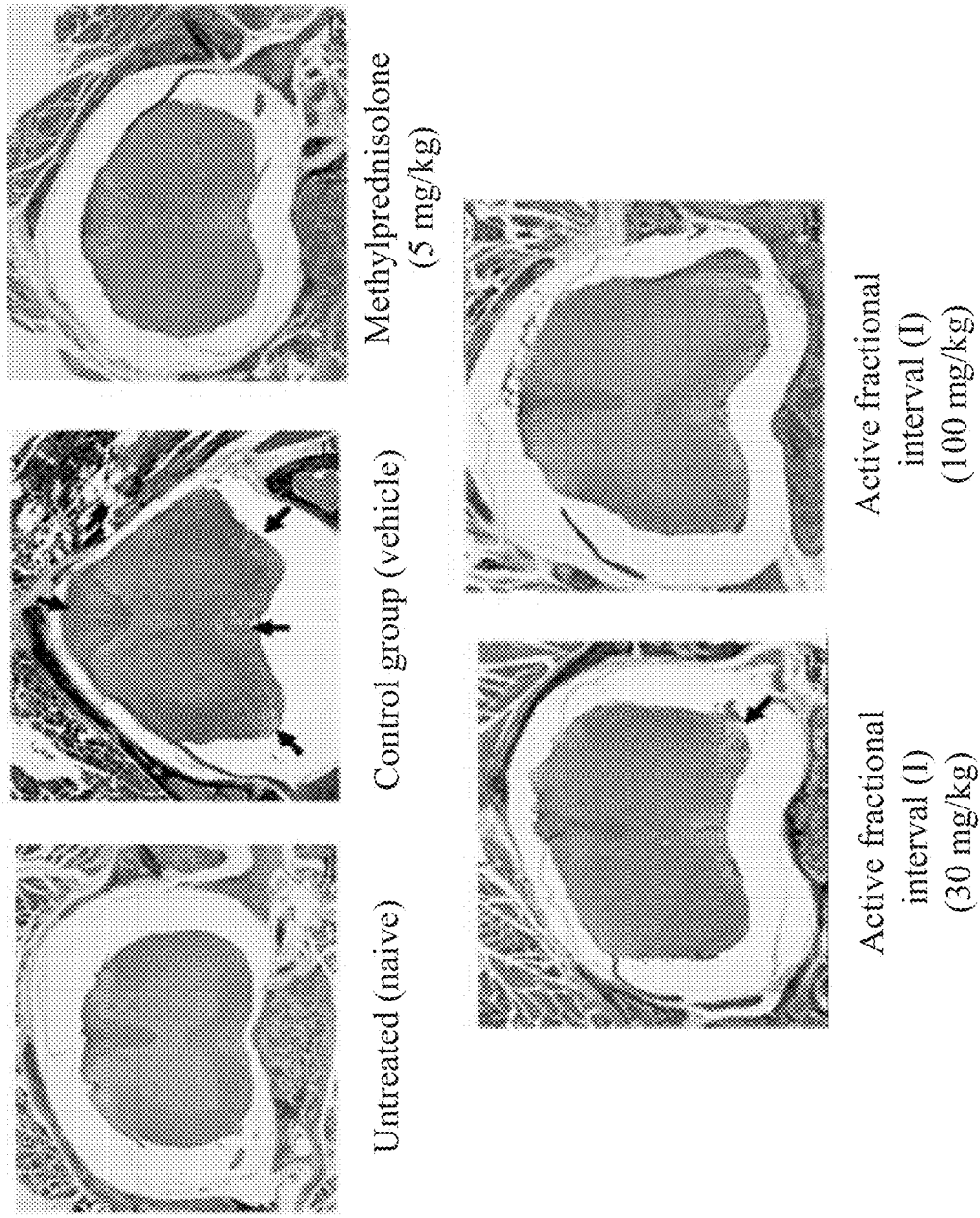

As shown in FIGS. 3A and 3B, after induction of EAE, the mice have been appeared the clinical symptoms of hind limb paralysis and severe forelimb weakness (such as Score 4 described above) on $14^{th}$ day after onset, but administration of the active fractional interval (I) of HE-06 with the concentration of 30 mg/kg and 100 mg/kg could significantly slow down the progress of EAE. In which * represents p value of less than 0.05;  represents p value of less than 0.01; * represents p value of less than 0.001.

Otherwise, Luxol fast blue (LFB) stain was performed to check the myelin of nerve tissue. Since myelin is a tubular sheath that is wrapped outside the axons of the neuronal cell, the integrity of the myelin under normal or pathological conditions can be observed by performing the myelin staining. As the histopathology staining pattern shown in FIG. 3C, the active fractional interval (I) of HE-06 could significantly improve the symptom of demyelination of cervical vertebrae in EAE animal model.

Moreover, the condition of the spinal cord was checked with the guidelines of Histopathological Lesion Severity Scores in the literature published by Shackelford et al. The histopathological grade and the degree of myelination damage of the spinal cord including cervical vertebrae, thoracic vertebrae and lumbar vertebrae were evaluated by a pathologic veterinarian. In which, the grade of histopathology is divided into five grades: Grade 1 represents the smallest damage (overall damage area <1%); Grade 2 represents minor damage (approximately 1-25% of total damage area); Grade 3 represents moderate Grade 4 represents moderate to severe injury (approximately 51-75% of total damage area); Grade 5 represents severe injury (approximately 76-100% of total damage area).

Figure 3D:
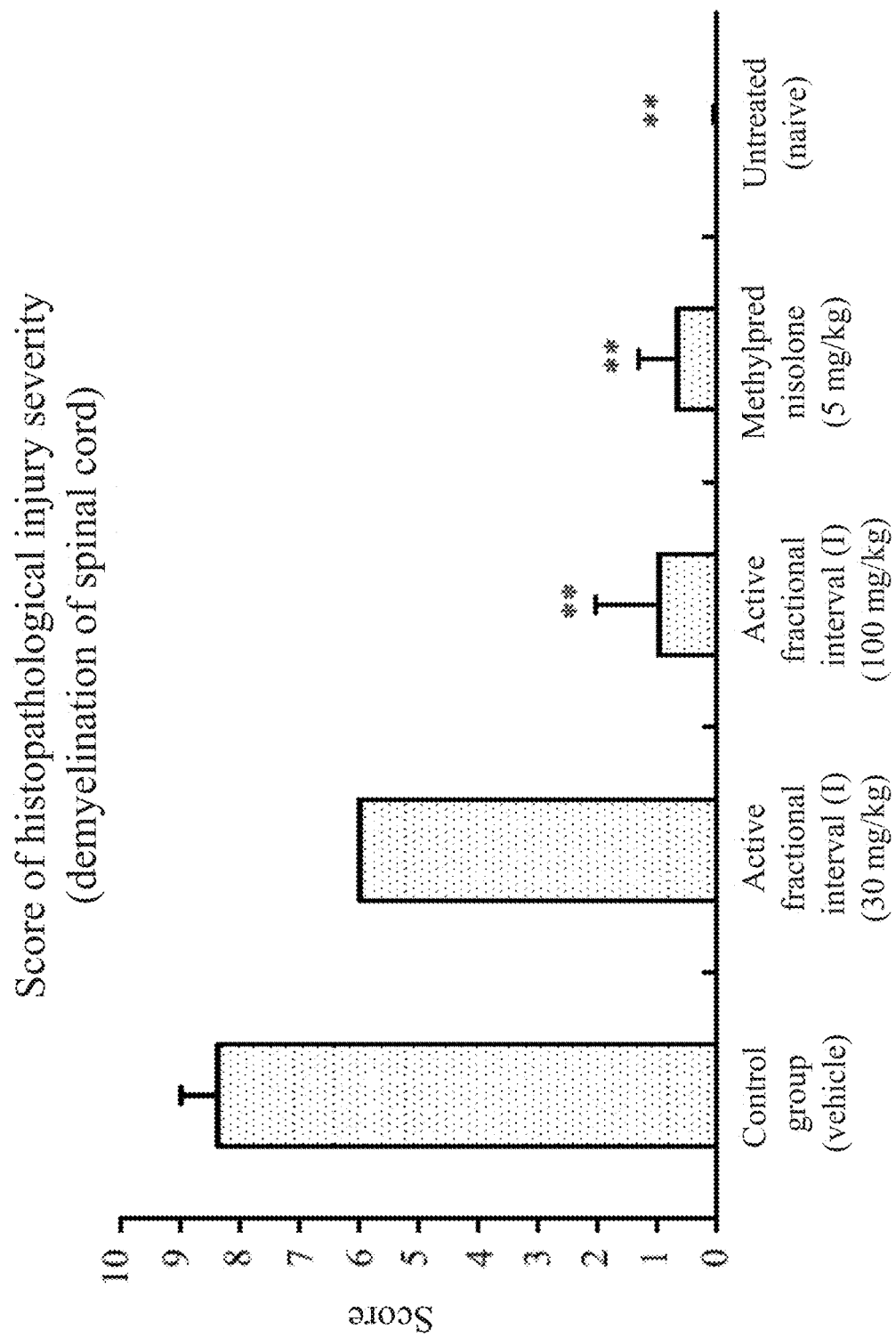
Figure 3E:
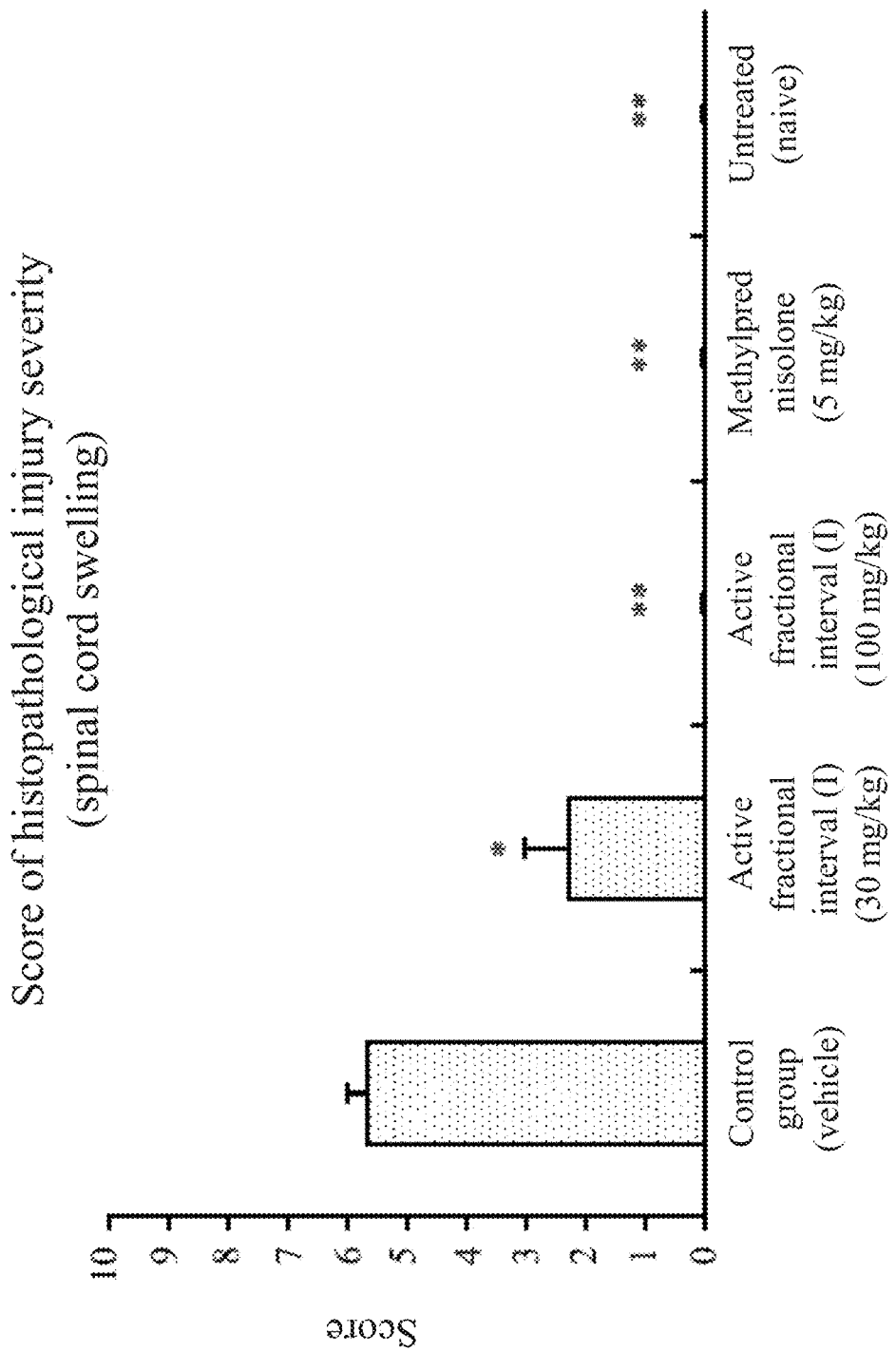

The observed and scored results were shown as FIGS. 3D and 3E. After induction of EAE, the mice have been to show the clinical symptoms of demyelination of spinal cord and axonal swelling on $14^{th}$ day after onset, but administering the active fractional interval (I) of HE-06 with the concentration of 30 mg/kg and 100 mg/kg could significantly reduce the degree of damage of the spinal cord in EAE animal model. In which * represents p value of less than 0.05; ** represents p value of less than 0.01.

Example 7: Purification and Preparation of the Active Fractional Interval (II) of HE-06

2.19 kg of HE-06 was taken to perform the extraction with 16 L methanol by heating and refluxing for 2 hours, and the extraction step was repeated twice to remove the dregs. The two extracts were then combined and concentrated to 100 mL, and 1900 mL of water was added to uniformly disperse the extract. Next, the extract was extracted with n-heptane and ethyl acetate twice, respectively, the ethyl acetate extract was concentrated to concrete type of 26.07 g, and 21.27 g of the ethyl acetate concrete was extracted by performing the solid phase adsorption extraction. Thereafter, 900 mL ethyl acetate solution with 80% n-heptane, 1800 mL ethyl acetate solution with 60% n-heptane, 3600 mL, ethyl acetate solution with 55% n-heptane, 900 mL ethyl acetate solution with 40% n-heptane, and 900 mL ethyl acetate solution were sequentially added to perform the elution. Every 900 mL was collected in a bottle and numbered No. 1~9, in which No. 3 was the active fractional interval (II) of HE-06.

Example 8: The Active Fractional Interval (11) of HE-06 can Inhibit IL-17 and TNF-α Secretion (1) Test of Inhibition in IL-17 Secretion Except for the drugs to be administered was replaced with the active fractional interval (II) of HE-06, the utilized EL4 lymphoma cells, the culture condition, and the detection method of IL-17 secretion are the same as described above, and will not repeat them here. The detected result of IL-17 secretion was shown in Table 2.

TABLE 2

The inhibitory effect of the active fractional interval (II) of HE-06 on IL-17 secretion in EL4 murine lymphoma cells. $IC_{50}$ is the concentration causing 50% IL-17 secretion inhibition.

| Test sample | $IC_{50}$ (μg/ml) |
|---|---|
| active fractional interval (II) of HE-06 | 17.4 |

The results of in vitro cell analysis shown in Table 2 indicated that the active fractional interval (II) of HE-06 can inhibit the secretion of IL-17 in activated EL4 lymphoma cells.

(2) Test of Inhibition in TNF-α Secretion

Except for the drugs to be administered was replaced with the active fractional interval (II) of HE-06, the utilized BALB/c mice, the feeding condition, the mouse model of acute inflammation, and the detection method of TNF-α secretion are the same as described above, and will not repeat them here. The detected result of TNF-α secretion was shown in FIG. 4A.

Figure 4A:
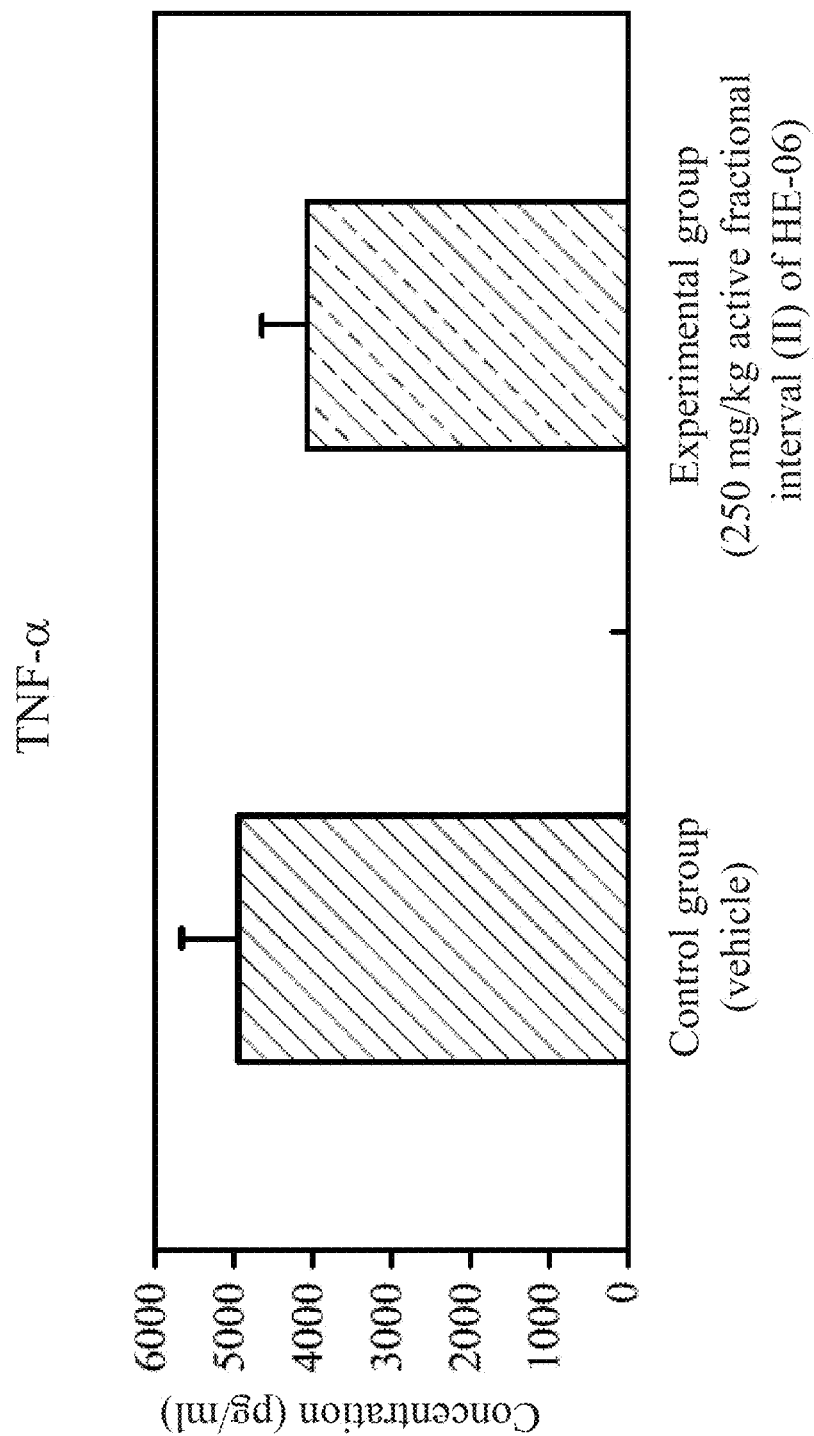
FIG. 4A-4C show the effects of active fractional interval (II) of Amomum tsao-ko extract HE-06 on inhibition of TNF-α secretion in LPS-induced acute inflammatory mouse model, delaying the progression of EAE mouse model, and slowing down the skin inflammatory conditions of IMQ-induced psoriasis-like dermatitis, respectively. In which * represents p value is less than 0.05;  represents p value is less than 0.01; * represents p value is less than 0.001.

As shown in FIG. 4A, the active fractional interval (II) of HE-06 could inhibit the secretion of TNF-α in LPS-induced acute inflammatory mice, and the inhibition level was about 16%, indicating that the active fractional interval (II) of HE-06 could in vivo inhibit TNF-α secretion induced by inflammation.

Example 9: The Active Fractional Interval (II) of HE-06 can Improve the Clinical Symptoms of EAE Except for the drugs to be administered was replaced with the active fractional interval (II) of HE-06 and the administered active fractional interval (II) of HE-06 with the concentration of 0 mg/kg (as the control group or vehicle), 30 mg/kg, 100 mg/kg and 300 mg/kg, the experimental animals, the established mouse autoimmune EAE model, and the scoring criteria are the same as described above, and will not repeat them here. The experimental results were shown in FIG. 4B, and the group to be administered with equal volume of solvent was considered as the control group.

Figure 4B:
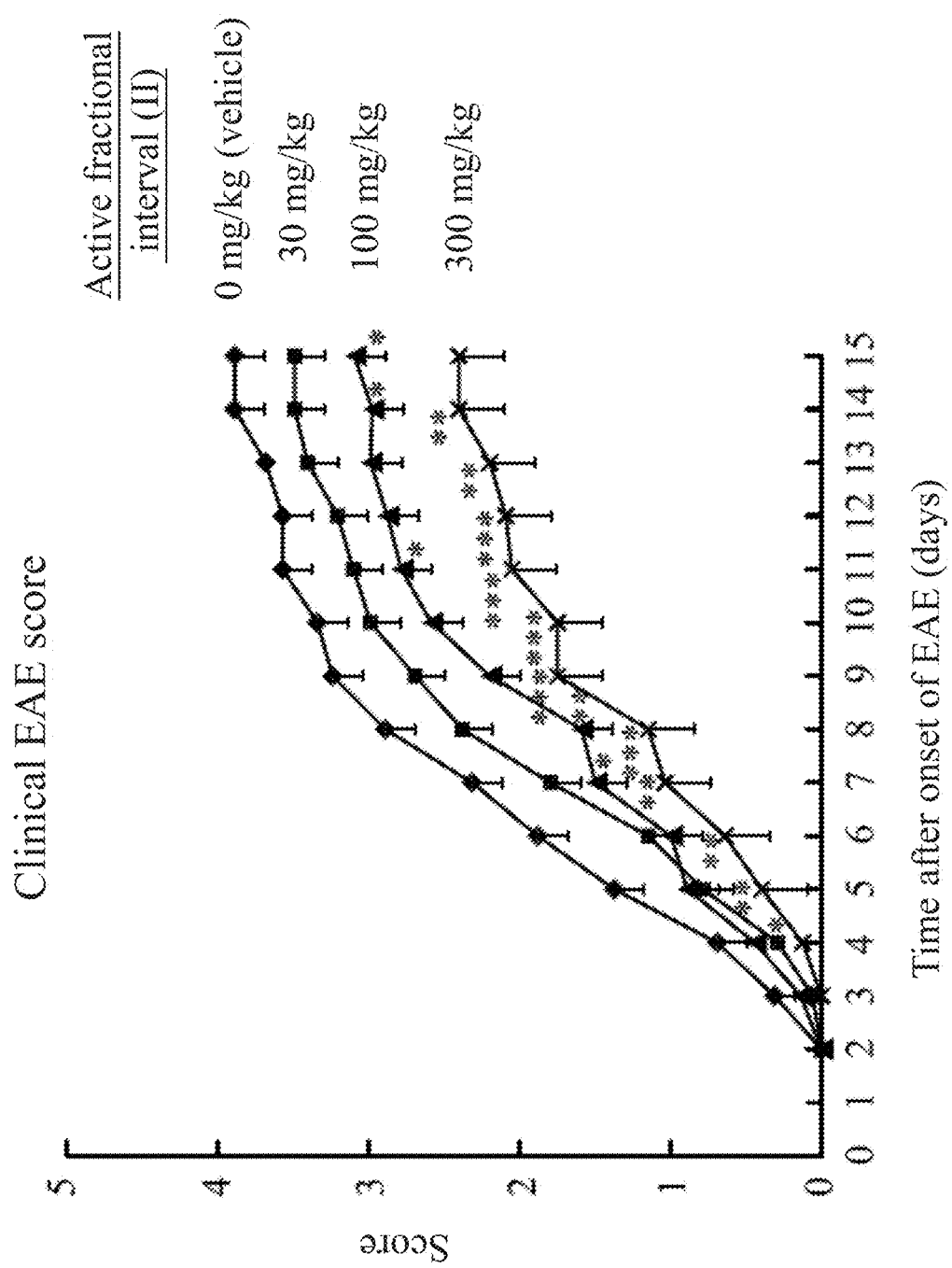

As shown in FIG. 4B, after induction of EAE, the mice have been appeared the clinical symptoms of hind limb paralysis and severe forelimb weakness as above described Score 4 on $14^{th}$ day after onset, but administration of the active fractional interval (II) of HE-06 with the concentration of 30 mg/kg, 100 mg/kg and 300 mg/kg could slow down the progress of EAE, and present a dose-dependent effect, indicating that the active fractional interval (II) of HE-06 can effectively improve the clinical symptoms in EAE animal model. In which * represents p value of less than 0.05;  represents p value of less than 0.01; * represents p value of less than 0.001.

Example 10: The Active Interval (II) of HE-06 can Alleviate the Symptom of Imiiquimod (IMQ)-Induced Psoriasis-Like Dermatitis (1) Experimental Animal The 8 weeks BALB/c male mice were purchased from BioLASCO Taiwan Co., Ltd. After acclimation and quarantine, the batch of mice were approximately 9-10 weeks of age at the time of performing the experiment of IMQ-induced psoriasis-like dermatitis. The experimental animals were bred in the environment: 12 hours light and 12 hours dark, room temperature of 23±2° C., and relative humidity of 40-70%. During feeding, animals were free to obtain adequate food and drinking water. In addition, during the quarantine and testing period, the animals were observed and recorded by the veterinarian and the experimental staff of ITRI to ensure health of these experimental animals.

(2) Establishment of Mouse Model of Psoriasis-Like Dermatitis

Before the experiment, the mice were weighed and grouped so that the average body weight of each group was not significantly different. Then, the hair on the back of each mouse was shaved, and the shaving area was about 4*2 $cm^2$. Since day 0, 3.125 mg imiquimod (IMQ) was administered by smearing to the skin of shaved area of each mouse daily for consecutive 6 days. At the same time, the active fractional interval (II) of HE-06 or solvent was also administered by performing tube feeding (10 ml/kg) or skin smearing (about 30~50 mg/mouse) for 6 days, and these mice were sacrificed on the $6^{th}$ day with excess $CO_2$.

(3) Records and Data Analysis of the Degree of Skin Irritation

The above-mentioned degree of skin irritation is based on Psoriasis Area and Severity Index (PAST), in which erythema, thickening, and scaling of skin were assessed and analyzed for judging the scale. Scale 0-4 is defined as follows: Scale 0 represents no obvious symptoms, Scale 1 represents mild symptoms, Scale 2 represents moderate symptoms, Scale 3 represents moderate to severe symptoms, and Scale 4 represents severe symptoms.

The mean value and standard error of mean (S.E.M.) of each group were calculated by accumulating the index observed in the same mouse, and t-test statistics was used to distinguish the differences between the groups. In which p value of less than 0.05 indicates that there exists a statistically significant difference between the two groups. The experimental results are shown in FIG. 4C.

Figure 4C:
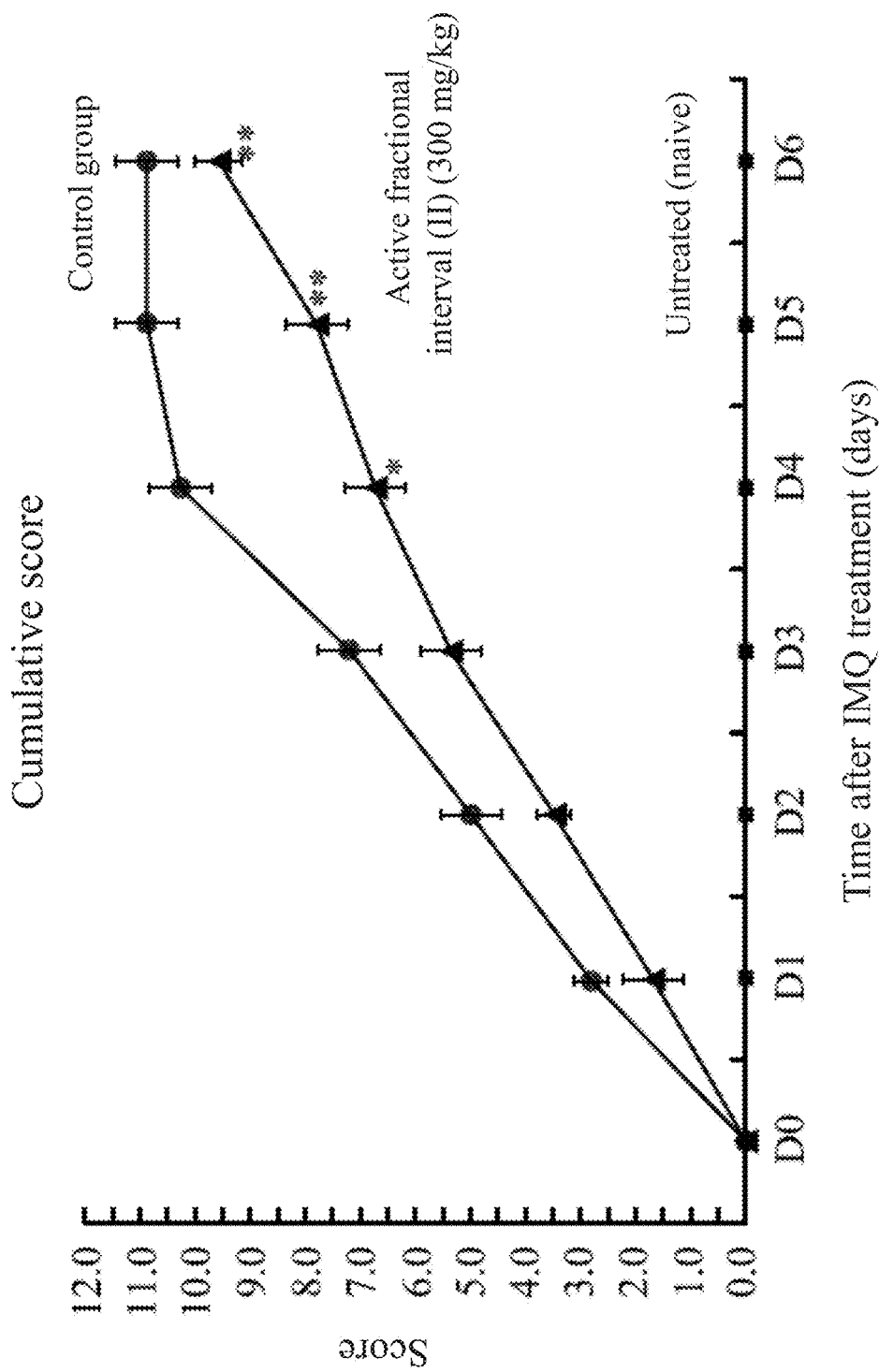

As shown in FIG. 4C, after induction of psoriasis-like dermatitis by IMQ, the mice have been appeared the clinical symptoms of psoriasis-like dermatitis on $2^{nd}$ day after induction, such as erythematous skin, uneven thickness, and wrinkled dander, but administration of the active fractional interval (II) of HE-06 could alleviate the clinical symptoms of IMQ-induced psoriasis-like dermatitis. In which * represents p value of less than 0.05; ** represents p value of less than 0.01.

Example 11: Isolation and Preparation of the Active Ingredient Compound, Vanillin or Tsaokoin (TK), of HE-06

The extract of A. tsao-ko, HE-06 was first extracted with a distillation step by steam for 24 hours to remove the portion of essential oil. Then, a step of heating and refluxing with a low polarity solvent was performed for 8 hours. Thereafter, the extract was eluted by gradient elution with n-Hexane, EtOAc and MeOH, and the step of Silica Gel Column Chromatography was further performed. Each fraction was analyzed and separated by TLC and the active fraction was checked by performing the activity test. Further, two compounds were isolated from the active fraction and determined to be vanillin and tsaokoin after analysis. Then, the fraction containing either vanillin or tsaokoin component was combined respectively to obtain the active ingredient compound vanillin and tsaokoin of HE-06.

Example 12: The Active Ingredient Compound Tsaokoin (TK) can Inhibit IL-17 and TNF-α Secretion (1) IL-17 Secretion and MTT Test Except for the drugs to be administered was replaced with active ingredient compound tsaokoin (TK) of HE-06, the utilized EL4 lymphoma cells, the culture condition, the method of inflammation induction, and the detection method of IL-17 secretion and MTT test are the same as described above, and will not repeat them here. The detected results of IL-17 secretion and MTT test were shown in FIG. 5A and Table 3.

TABLE 3

The inhibitory effect of the active ingredient compound TK on IL-17 secretion in EL4 murine lymphoma cells. $IC_{50}$ is the concentration of TK causing 50% IL-17 secretion inhibition.

| Test sample | $IC_{50}$ (μg/ml) |
| --- | --- |
| Tsaokoin (TK) | 12.1 |

Figure 5A:
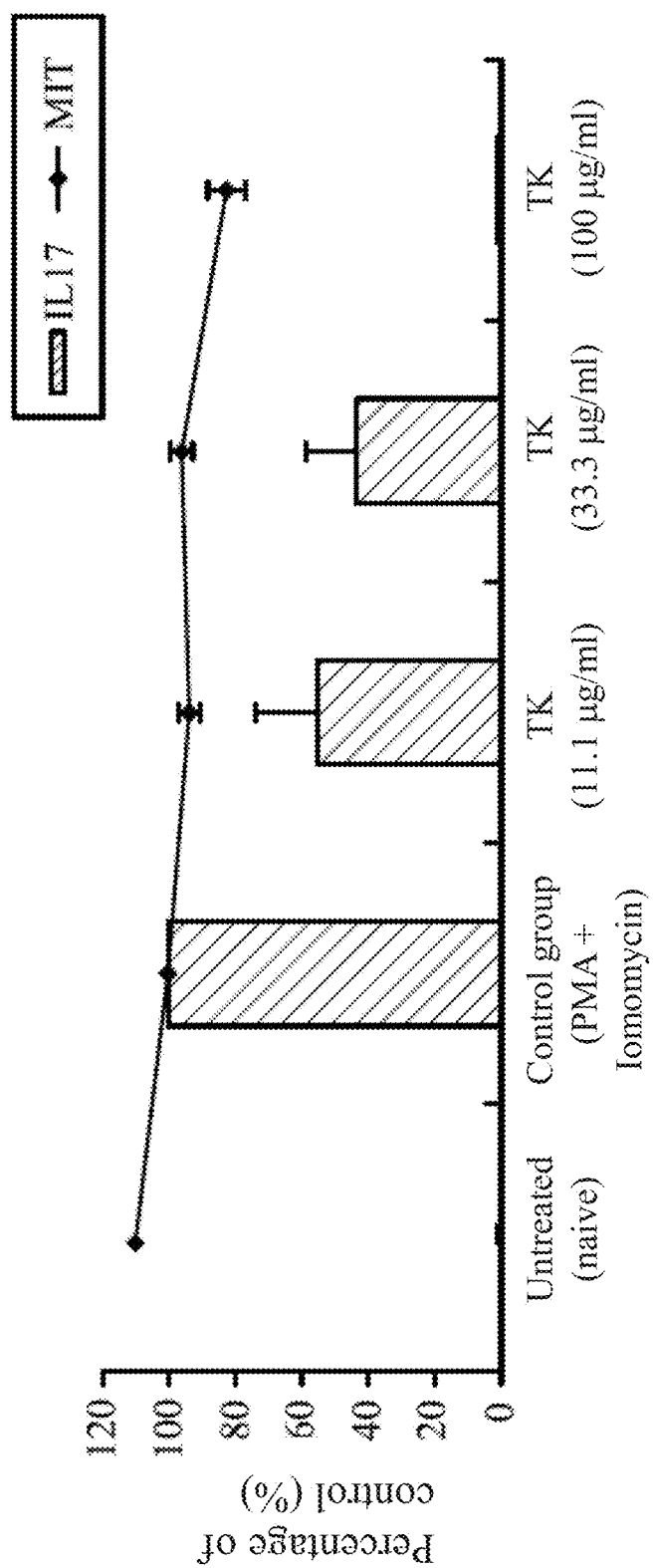
FIG. 5A-5D show the effects of active ingredient Tsaokoin (TK) of Amomum tsao-ko extract HE-06 on inhibiting IL-17 secretion of induced EL4 lymphoma cells, inhibiting TNF-α secretion in LPS-induced acute inflammatory mouse model, delaying the progression of EAE mouse model, and slowing down the skin inflammatory conditions of IMQ-induced psoriasis-like dermatitis, respectively. In which * represents p value is less than 0.05;  represents p value is less than 0.01; * represents p value is less than 0.001.

The results of in vitro cell analysis shown in FIG. 5A indicated that the active ingredient compound TK of HE-06 can inhibit the secretion of IL-17 in activated EL4 lymphoma cells.

(2) Test of Inhibition in TNF-α Secretion

Except for the drugs to be administered was replaced with the active ingredient compound tsaokoin (TK) of HE-06, the utilized BALB/c mice, the feeding condition, the mouse model of acute inflammation, and the detection method of TNF-α secretion are the same as described above, and will not repeat them here. The detected result of TNF-α secretion was shown in FIG. 5B.

Figure 5B:
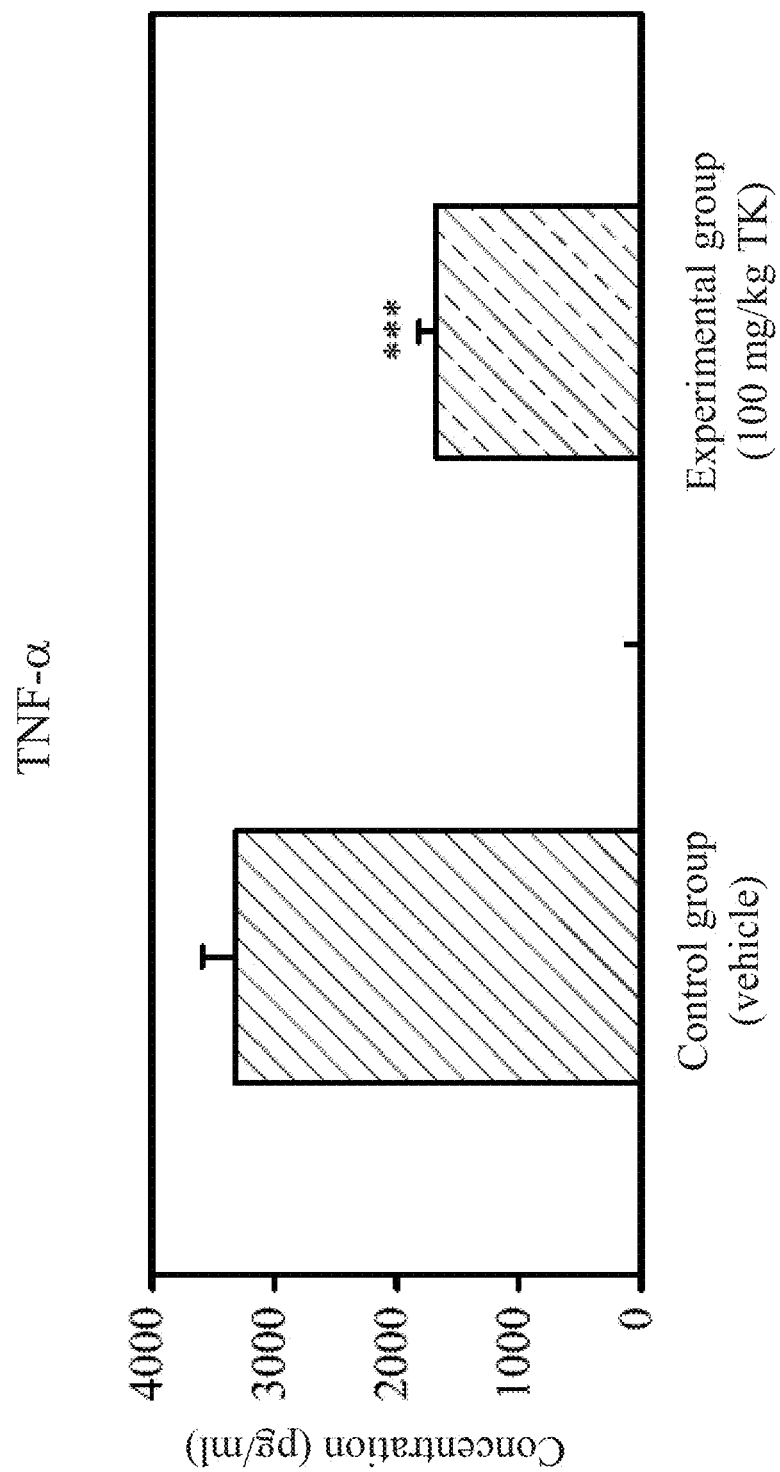

As shown in FIG. 5B, the active ingredient compound tsaokoin (TK) of HE-06 could significantly inhibit the secretion of TNF-α in LPS-induced acute inflammatory mice, indicating that TK could in vivo inhibit TNF-α secretion induced by inflammation. In which *** represents p value of less than 0.001.

Example 13: The Active Ingredient Compound Tsaokoin (TK) can Improve the Clinical Symptoms of EAE Except for the drugs to be administered was replaced with the active ingredient compound tsaokoin (TK) of HE-06 and the administered tsaokoin with the concentration of 0 mg/kg (as the control group or vehicle), 30 mg/kg, and 100 mg/kg, the experimental animals, the established mouse autoimmune EAE model, and the scoring criteria are the same as described above, and will not repeat them here. The experimental results were shown in FIG. 5C, and the group to be administered with equal volume of solvent was considered as the control group.

Figure 5C:
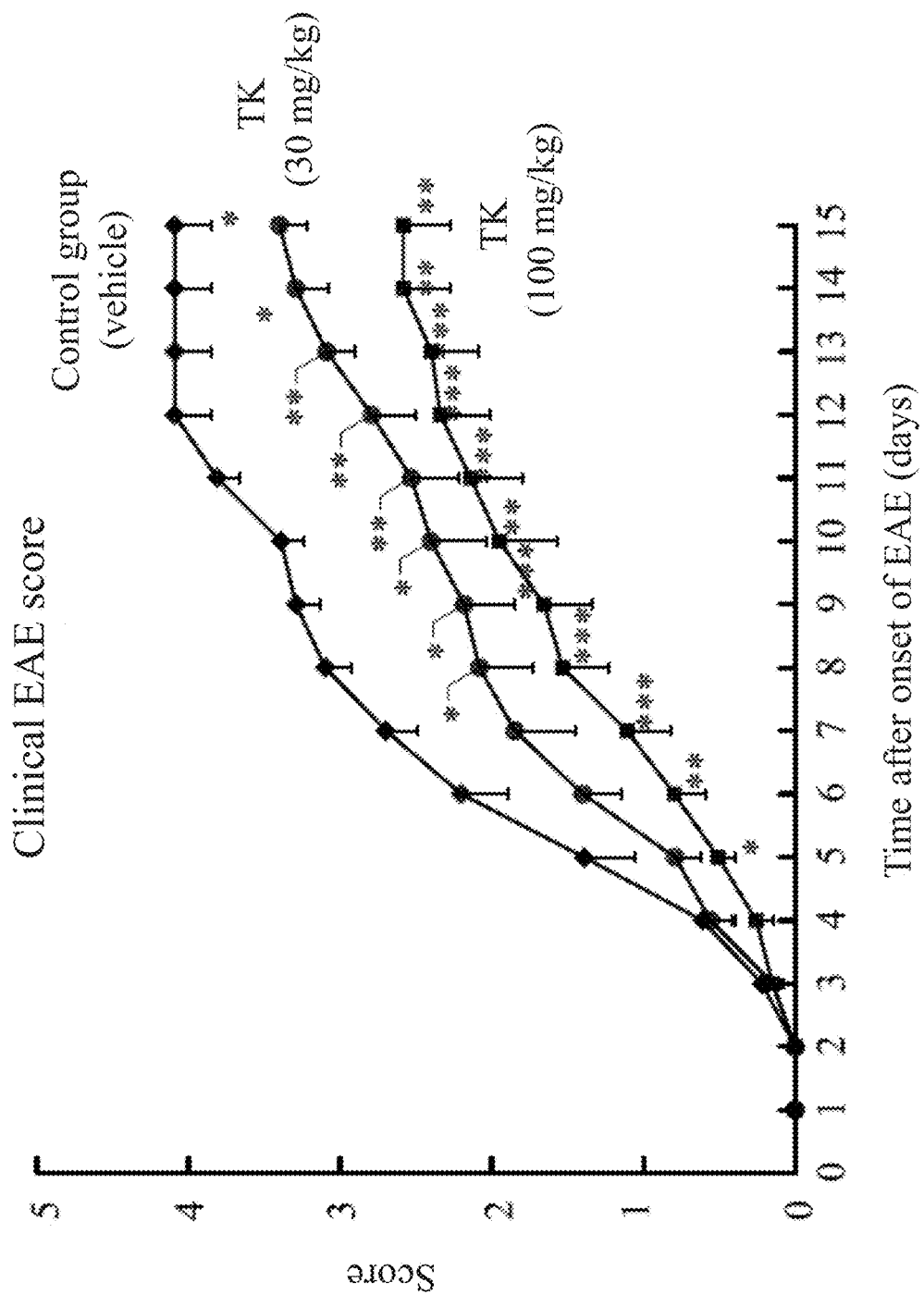

As shown in FIG. 5C, after induction of EAE, the mice have been appeared the clinical symptoms of hind limb paralysis and severe forelimb weakness as above described Score 4 on $14^{th}$ day after onset, but administration of tsaokoin with the concentration of 30 mg/kg and 100 mg/kg could slow down the progress of EAE, and present a dose-dependent effect, indicating that tsaokoin can effectively improve the clinical symptoms in EAE animal model. In which * represents p value of less than 0.05;  represents p value of less than 0.01; * represents p value of less than 0.001.

Example 14: The Active Ingredient Compound Tsaokoin (TK) can Alleviate the Symptom of Imiquimod (IMQ)-Induced Psoriasis-Like Dermatitis Except for the drugs to be administered was replaced with the active ingredient compound tsaokoin (TK) of HE-06 and the administered tsaokoin with the concentration of 100 mg/kg, the experimental animals, the established model of psoriasis-like dermatitis, and the scoring criteria are the same as described above, and will not repeat them here. The experimental results were shown in FIG. 5D, and the group to be administered with equal volume of solvent was considered as the control group.

Figure 5D:
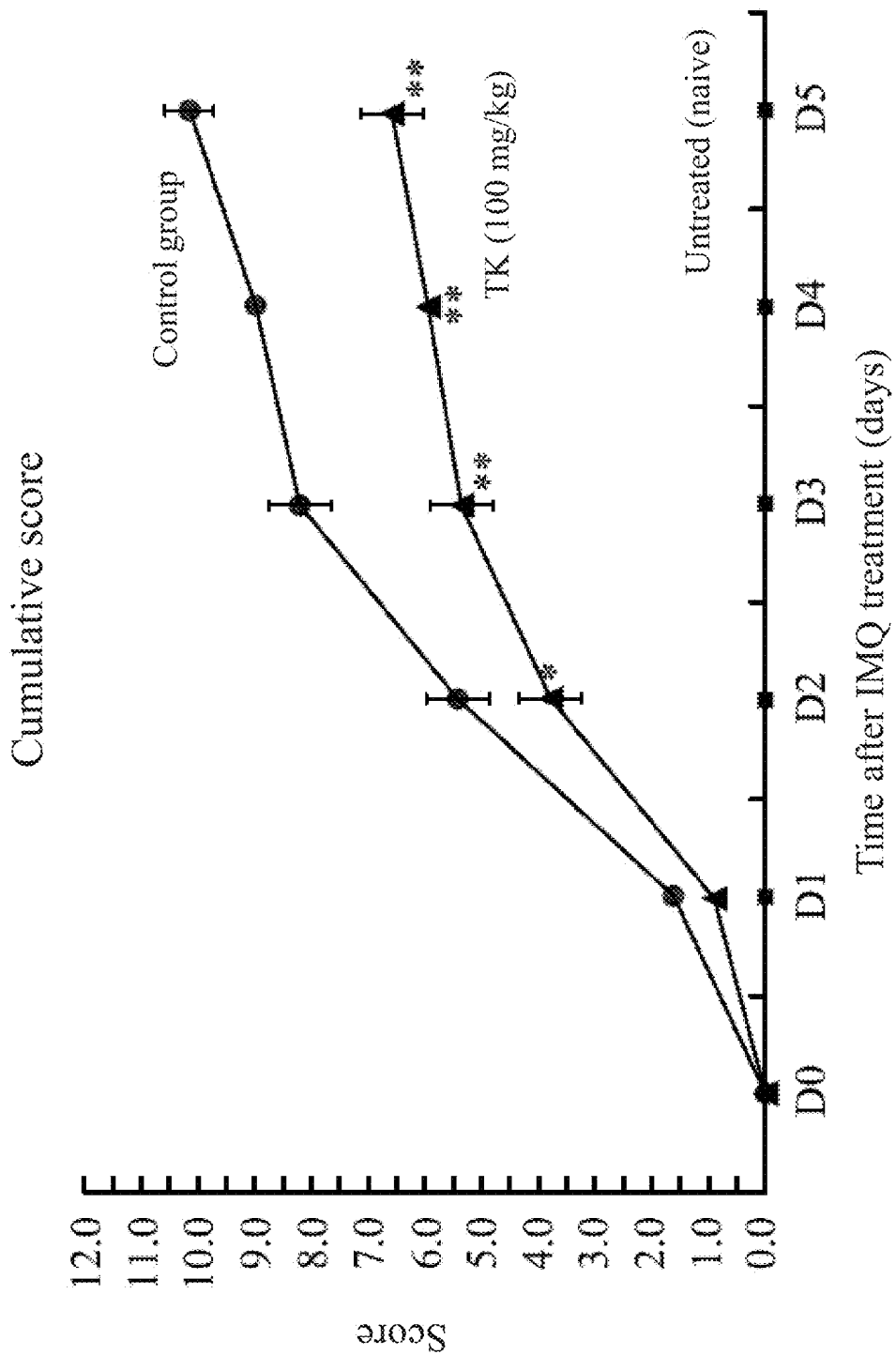

As shown in FIG. 5D, after induction of psoriasis-like dermatitis by IMQ, the mice have been appeared the clinical symptoms of psoriasis-like dermatitis on $2^{nd}$ day after induction, such as erythematous skin, uneven thickness, and wrinkled dander, but administration of tsaokoin could significantly alleviate the clinical symptoms of IMQ-induced psoriasis-like dermatitis. In which * represents p value of less than 0.05; ** represents p value of less than 0.01.

It will be apparent to those skilled in the art that various modifications and variations can be made to the disclosed embodiments. It is intended that the specification and examples be considered as exemplary only, with a true scope of the disclosure being indicated by the following claims and their equivalents.

What is claimed is:

1. A method of treating or alleviating Multiple Sclerosis (MS), comprising:
   administering a pharmaceutical composition to a subject in need thereof, wherein the pharmaceutical composition comprises an extract of Amomum tsao-ko extracted by only 50-95% ethanol and a pharmaceutically acceptable carrier or salt,
   an effective ingredient of the extract of Amomum tsao-ko comprises vanillin and tsaokoin,
   wherein a volume of the ethanol is 3-10 times the weight of Amomum tsao-ko, and
   wherein the extraction of the extract of Amomum tsao-ko is performed at an extraction temperature of 10 to 35° C. and an extraction time of 3 to 10 days.

2. The method of treating or alleviating Multiple Sclerosis (MS) as claimed in claim 1, wherein the extract of Amomum tsao-ko is extracted from a root, a stem, a leaf, a flower, a fruit, a seed, or a combination thereof.

3. The method of treating or alleviating Multiple Sclerosis (MS) as claimed in claim 1, wherein the pharmaceutical composition has the effect of inhibiting cytokine secretion, and the cytokine includes IL-17, TNF-α, or a combination thereof.

4. The method of treating or alleviating Multiple Sclerosis (MS) as claimed in claim 1, wherein the pharmaceutical composition is administered orally, non-orally, parenterally by an inhalation spray, or via an implanted reservoir.

* * * * *